US007509174B2

(12) United States Patent
Imran et al.

(10) Patent No.: US 7,509,174 B2
(45) Date of Patent: Mar. 24, 2009

(54) GASTRIC TREATMENT/DIAGNOSIS DEVICE AND ATTACHMENT DEVICE AND METHOD

(75) Inventors: Mir A. Imran, Los Altos Hills, CA (US); Olivier K. Colliou, Los Gatos, CA (US); Ted W. Layman, Menlo Park, CA (US); Deepak R. Gandhi, San Jose, CA (US); Sharon L. Lake, Menlo Park, CA (US)

(73) Assignee: IntraPace, Inc., Menlo Park, CA (US)

( * ) Notice: Subject to any disclaimer, the term of this patent is extended or adjusted under 35 U.S.C. 154(b) by 1016 days.

(21) Appl. No.: 10/295,128

(22) Filed: Nov. 14, 2002

(65) Prior Publication Data
US 2003/0167025 A1 Sep. 4, 2003

Related U.S. Application Data

(62) Division of application No. 09/847,884, filed on May 1, 2001, now Pat. No. 6,535,764.

(51) Int. Cl.
*A61N 1/05* (2006.01)
*A61B 5/103* (2006.01)
(52) U.S. Cl. .................... 607/133; 607/40; 600/593; 604/516
(58) Field of Classification Search .......... 607/40, 607/133, 149; 600/373, 593
See application file for complete search history.

(56) References Cited

U.S. PATENT DOCUMENTS 3,411,507 A 11/1968 Wingrove ............... 128/422

(Continued)

FOREIGN PATENT DOCUMENTS

EP 0129483 12/1984 ............... 1/36

(Continued)

OTHER PUBLICATIONS

H. Geldof, et al., Electrogastrographic Study of Gastric Myoelectrical Activity In Patients With Unexplained Nausea And Vomiting, *Gut*, 27:799-808, (1986).

(Continued)

*Primary Examiner*—Carl H Layno
*Assistant Examiner*—Natasha N Patel
(74) *Attorney, Agent, or Firm*—Townsend and Townsend and Crew LLP

(57) ABSTRACT

A device, system and method for diagnosing and treating gastric disorders is provided. A functional device resides within the patient's stomach and is secured to the stomach wall by an attachment device. The functional device may be a sensor for sensing various parameters of the stomach or stomach environment, or may be a therapeutic delivery device. The functional device in one embodiment provides a device, system and method for gastric electrical stimulation where stimulating electrodes are secured to the wall of the stomach by the attachment device or otherwise. A preferred device includes: at least one stimulating electrode in electrical contact with the stomach wall; an electronics unit containing the electronic circuitry of the device; and an attachment mechanism for attaching the device to the stomach wall. The functional devices may be programmed to respond to sensed information or signals. An endoscopic delivery system delivers the functional device through the esophagus and into the stomach where it is attached the stomach wall. The endoscopic instruments attach or remove the attachment devices and functional devices from the stomach and may be used to assist in determining the optimal attachment location.

14 Claims, 24 Drawing Sheets

U.S. PATENT DOCUMENTS

| | | | | |
|---|---|---|---|---|
| 3,646,940 | A | | 3/1972 | Timm et al. ............... 128/421 |
| 3,662,758 | A | | 5/1972 | Glover ...................... 128/419 |
| 3,677,251 | A | | 7/1972 | Bowers ...................... 128/419 |
| 3,735,766 | A | | 5/1973 | Bowers et al. ............. 128/419 |
| 3,796,221 | A | | 3/1974 | Hagfors ..................... 128/421 |
| 3,815,611 | A | | 6/1974 | Denniston, III ............ 128/419 |
| 3,835,864 | A | * | 9/1974 | Rasor et al. ................ 607/36 |
| 3,835,865 | A | | 9/1974 | Bowers ...................... 128/419 |
| 4,102,344 | A | | 7/1978 | Conway et al. ............. 128/419 |
| RE30,366 | E | | 8/1980 | Rasor et al. ................ 128/419 |
| 4,628,928 | A | | 12/1986 | Lowell ....................... 128/303 |
| 4,823,808 | A | | 4/1989 | Clegg et al. ................ 128/773 |
| 4,921,481 | A | | 5/1990 | Danis et al. ................ 604/67 |
| 4,925,446 | A | | 5/1990 | Garay et al. ................ 604/96 |
| 5,144,952 | A | * | 9/1992 | Frachet et al. ............. 600/379 |
| 5,188,104 | A | | 2/1993 | Wernicke et al. ........... 128/419 |
| 5,197,491 | A | | 3/1993 | Anderson et al. .......... 128/786 |
| 5,217,449 | A | | 6/1993 | Yuda et al. ................. 604/890 |
| 5,292,344 | A | * | 3/1994 | Douglas ..................... 607/40 |
| 5,415,181 | A | | 5/1995 | Hogrefe et al. ............ 128/736 |
| 5,423,872 | A | | 6/1995 | Cigaina ...................... 607/40 |
| 5,540,730 | A | | 7/1996 | Terry et al. ................. 607/40 |
| 5,558,640 | A | | 9/1996 | Pfeiler et al. ............... 604/67 |
| 5,690,691 | A | | 11/1997 | Chen et al. .................. 607/40 |
| 5,716,392 | A | | 2/1998 | Bourgeois et al. .......... 607/132 |
| 5,766,234 | A | * | 6/1998 | Chen et al. .................. 607/92 |
| 5,792,048 | A | | 8/1998 | Schaefer ..................... 600/302 |
| 5,800,445 | A | | 9/1998 | Ratcliff et al. ............. 606/116 |
| 5,836,994 | A | | 11/1998 | Bourgeois ................... 607/40 |
| 5,861,014 | A | | 1/1999 | Familoni ..................... 607/40 |
| 5,928,195 | A | | 7/1999 | Malamud et al. ........... 604/141 |
| 5,993,473 | A | * | 11/1999 | Chan et al. .................. 606/192 |
| 5,995,872 | A | | 11/1999 | Bourgeois ................... 607/40 |
| 6,026,326 | A | | 2/2000 | Bardy ......................... 607/40 |
| 6,041,258 | A | | 3/2000 | Cigaina et al. .............. 607/40 |
| 6,083,249 | A | | 7/2000 | Familoni ..................... 607/40 |
| 6,091,992 | A | | 7/2000 | Bourgeois et al. .......... 607/40 |
| 6,097,984 | A | | 8/2000 | Douglas ..................... 607/40 |
| 6,098,629 | A | | 8/2000 | Johnson et al. ............. 128/897 |
| 6,104,955 | A | | 8/2000 | Bourgeois ................... 607/40 |
| 6,115,635 | A | | 9/2000 | Bourgeois ................... 607/40 |
| 6,183,411 | B1 | * | 2/2001 | Mortier et al. .............. 600/16 |
| 6,205,359 | B1 | | 3/2001 | Boveja ........................ 607/45 |
| 6,216,039 | B1 | | 4/2001 | Bourgeois ................... 607/40 |
| 6,243,607 | B1 | | 6/2001 | Mintchev et al. ........... 607/40 |
| 6,285,897 | B1 | | 9/2001 | Kilcoyne et al. | |
| 6,321,124 | B1 | | 11/2001 | Cigaina ...................... 607/133 |
| 6,327,503 | B1 | | 12/2001 | Familoni ..................... 607/40 |
| 6,366,814 | B1 | | 4/2002 | Boveja et al. ............... 607/45 |
| 6,381,495 | B1 | | 4/2002 | Jenkins ....................... 607/40 |
| 6,427,089 | B1 | | 7/2002 | Knowlton | |
| 6,449,511 | B1 | | 9/2002 | Mintchev et al. ........... 607/40 |
| 6,453,199 | B1 | | 9/2002 | Kobozev ..................... 607/40 |
| 6,454,785 | B2 | | 9/2002 | De Hoyos Garza | |
| 6,477,423 | B1 | | 11/2002 | Jenkins ....................... 607/40 |
| 6,510,332 | B1 | | 1/2003 | Greenstein .................. 600/377 |
| 6,529,778 | B2 | | 3/2003 | Prutchi ....................... 607/119 |
| 6,540,789 | B1 | | 4/2003 | Silverman et al. ......... 623/23.65 |
| 6,542,776 | B1 | * | 4/2003 | Gordon et al. .............. 607/40 |
| 6,564,101 | B1 | | 5/2003 | Zikria ......................... 607/40 |
| 6,571,127 | B1 | | 5/2003 | Ben-Haim et al. .......... 607/40 |
| 6,591,137 | B1 | | 7/2003 | Fischell et al. .............. 607/40 |
| 6,600,953 | B2 | | 7/2003 | Flesler et al. ................ 607/40 |
| 6,606,518 | B1 | | 8/2003 | Cigaina ...................... 607/41 |
| 6,606,523 | B1 | | 8/2003 | Jenkins ....................... 607/133 |
| 6,609,025 | B2 | | 8/2003 | Barrett et al. ............... 607/2 |
| 6,611,715 | B1 | | 8/2003 | Boveja ........................ 607/40 |
| 6,615,084 | B1 | | 9/2003 | Cigaina ...................... 607/40 |
| 6,684,104 | B2 | | 1/2004 | Gordon et al. .............. 607/40 |
| 6,689,056 | B1 | * | 2/2004 | Kilcoyne et al. ............ 600/300 |
| 6,826,428 | B1 | | 11/2004 | Chen et al. .................. 607/40 |
| 6,879,859 | B1 | | 4/2005 | Boveja ........................ 607/45 |
| 6,895,278 | B1 | | 5/2005 | Gordon ....................... 607/40 |
| 6,895,279 | B2 | | 5/2005 | Loeb et al. .................. 607/40 |
| 2002/0072780 | A1 | | 6/2002 | Folby .......................... 607/40 |
| 2002/0103424 | A1 | * | 8/2002 | Swoyer et al. .............. 600/350 |
| 2002/0103521 | A1 | | 8/2002 | Swoyer et al. .............. 607/116 |
| 2002/0103522 | A1 | | 8/2002 | Swoyer et al. .............. 607/116 |
| 2002/0161414 | A1 | | 10/2002 | Flesler et al. ................ 607/40 |
| 2002/0198570 | A1 | | 12/2002 | Puskas ........................ 607/40 |
| 2003/0055463 | A1 | * | 3/2003 | Gordon et al. .............. 607/40 |
| 2003/0212439 | A1 | | 11/2003 | Schuler et al. .............. 607/40 |
| 2004/0059393 | A1 | | 3/2004 | Policker et al. ............. 607/40 |
| 2004/0133089 | A1 | | 7/2004 | Kilcoyne et al. ............ 600/350 |
| 2004/0147816 | A1 | | 7/2004 | Policker et al. ............. 600/300 |
| 2004/0162595 | A1 | | 8/2004 | King ........................... 607/40 |
| 2005/0021101 | A1 | | 1/2005 | Chen et al. .................. 607/40 |
| 2005/0113880 | A1 | | 5/2005 | Gordon et al. .............. 436/106 |

FOREIGN PATENT DOCUMENTS

| | | | |
|---|---|---|---|
| EP | 0571938 | 4/1999 | ................ 1/36 |
| WO | WO 98/43700 | 10/1998 | |
| WO | 9853878 | 12/1998 | ................ 1/5 |
| WO | WO 00/30534 | 6/2000 | |
| WO | WO0176690 | 10/2000 | |
| WO | 0158389 | 8/2001 | ................ 2/48 |
| WO | 0176690 | 10/2001 | ................ 1/18 |
| WO | WO 02/26101 A2 | 4/2002 | |

OTHER PUBLICATIONS

Brent W. Miedema, et al., Pacing The Human Stomach, *Surgery*, 143-150, (Feb. 1992).

Keith A. Kelly, Differential Responses Of The Canine Gastric Corpus And Antrum To Electric Stimulation, *Am. J. of Physiology*, 226/1:230-234, (Jan. 1974).

Electric Stimulation of the Gastrointestinal Tract, GP, p. 151 (Apr. 1964).

Michael P. Hocking, Postoperative Gastroparesis And Tachygastria-Response to Electric Stimulation and Erythromycin, *Surgery*, 114/3:538-542 (Sep. 1993).

Keith A. Kelly et al., Role of the Gastric Pacesetter Potential Defined by Electrical Pacing, *Canadian J. of Physiology and Pharmacology*, 50:1017-1019, (1972).

Babajide O. Familoni, Efficacy of Electrical Stimulation at Frequencies Higher Than Basal Rate in Canine Stomach, *Digestive Diseases and Sciences*, 42/5:892-897, (May 1997).

Bader-Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767-G774, (Oct. 1993).

Babajide O. Familoni, et al., Electrical Pacing of the Stomach in Dogs.

S. K. Sarna, et al., Electrical Stimulation of Gastric Electrical Control Activity, *Am. J. of Physiology*, 225/1:125-131, (Jul. 1973).

S. K. Sarna, et al., Gastric Pacemakers, *Gastroenterology*, 70:226-231, (1976).

Edwin E. Daniel, et al., Electrical Activity of the Gastrointestinal Tract as an Indication of Mechanical Activity, *Am. J. of Digestive Diseases*, 8/1:54-102, (1963).

C. Paul Swain, et al., An Endoscopically Deliverable Tissue-Transfixing Device For Securing Biosensors In The Gastrointestinal Tract, *Gastrointestinal Endoscopy*, 40/6:730-734 (1994).

Keith E. Kelly, et al., Pacing The Canine Stomach With Electric Stimulation, *Am. J. of Physiology*, 222/3:588-594 (Mar. 1972).

J. Chris Eagon et al., Gastrointestinal Pacing, *Surgical Clinics of North America* 73/6:1161-1172 (Dec. 1993).

Valerio Cigaina, et al., Gastric Myo-Electrical Pacing As Therapy For Morbid Obesity: Preliminary Results.

M. Kubota, et al., Manometric Evaluation of Children With Chronic Constipation Using a Suction-Stimulating Electrode, Eur. J. Pediatr. Surg., 2:287-290, (1992).

* cited by examiner

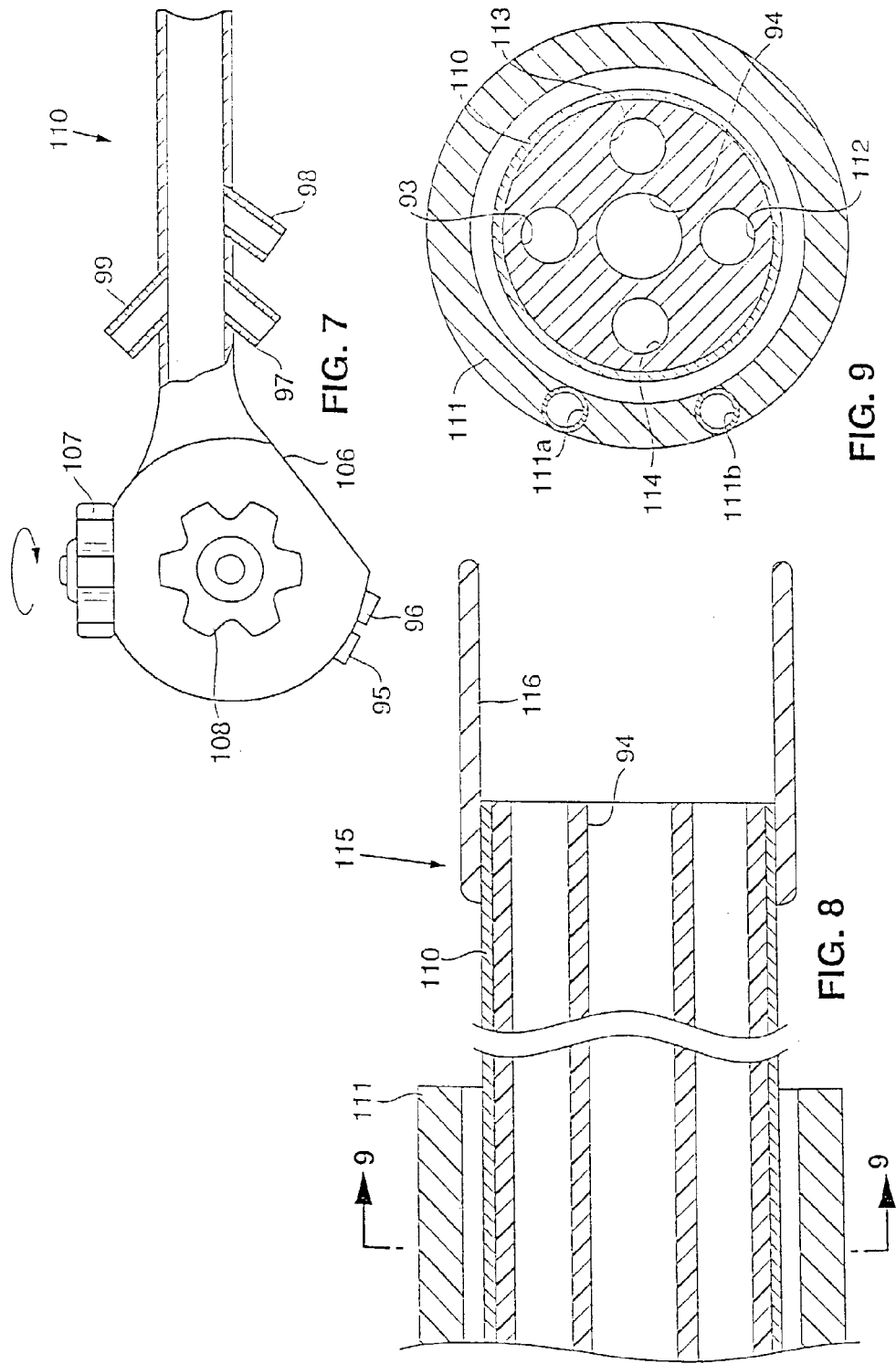

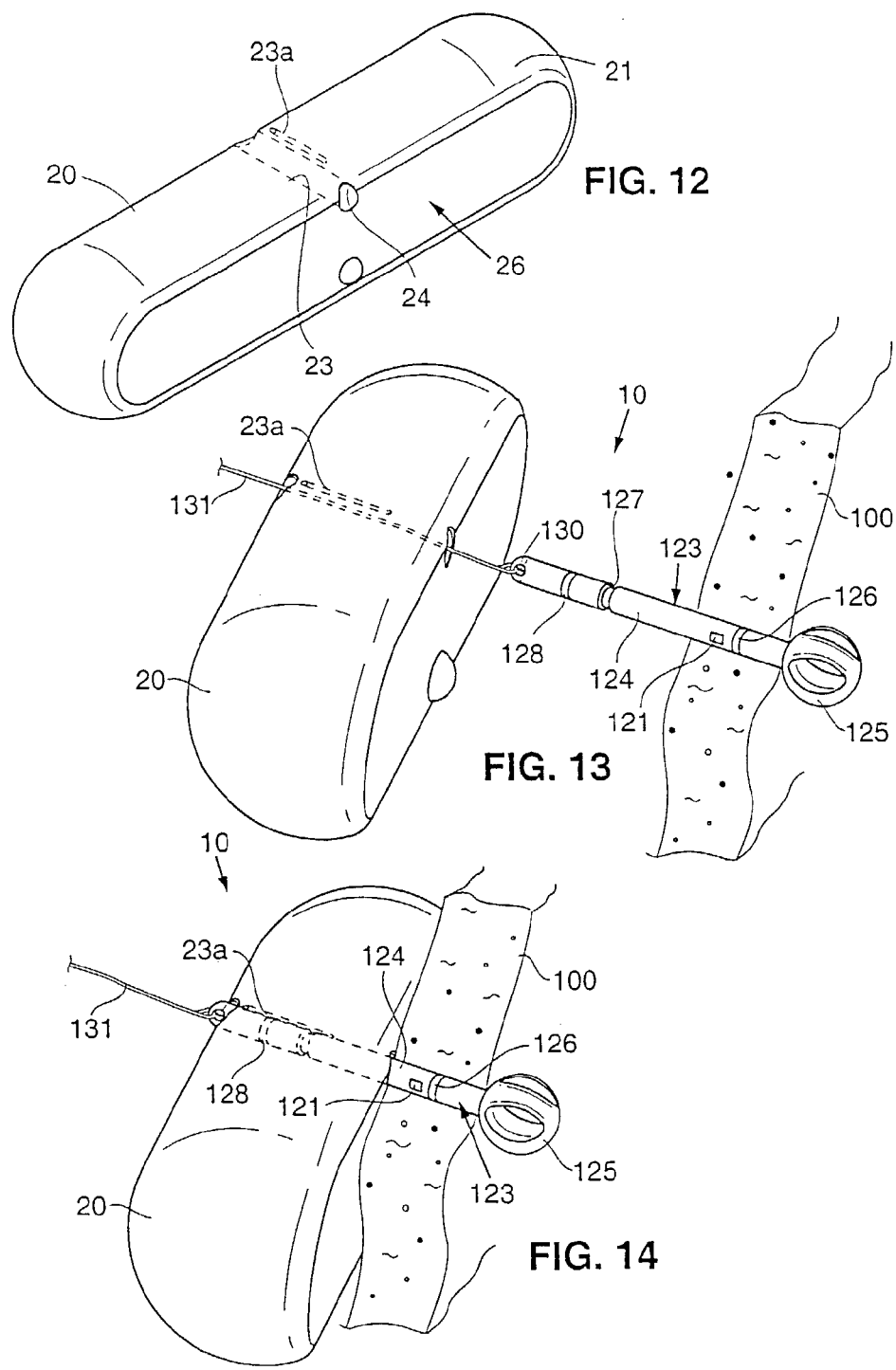

GASTRIC TREATMENT/DIAGNOSIS DEVICE AND ATTACHMENT DEVICE AND METHOD

This application is a Divisional of application Ser. No. 09/847,884 filed May 1, 2001 now U.S. Pat. No. 6,535,764.

FIELD OF THE INVENTION

This invention relates to an implantable device, system and method for electrically stimulating the stomach wall to effect gastric motility or otherwise treat gastrointestinal related disorders.

BACKGROUND OF THE INVENTION

Various organs of the gastrointestinal tract such as the stomach, small intestine and colon contain cells that are believed to govern the organs' periodic contractile behavior. In healthy humans, in certain regions of the organs, these cells generate and propagate rhythmic electrical signals. In general, several types of electrical potential activity have been observed in the gastrointestinal tract. Consistent slow wave or pacesetter potentials have been observed and higher frequency spike activity has been observed. The pacesetter potentials are continuously propagating, relatively low frequency, cyclic depolarizations of the smooth muscle cell lining. The higher frequency spike bursts correspond to some extent with smooth muscle contractile activity and peristalsis. In general, when the spike burst activity occurs, it appears to be at a fixed time delay with respect to the slow wave potentials. It is believed that when the pacesetter potentials are combined with a chemical or neural excitation of the cells that smooth muscle contractile activity occurs. Also it is believed that the pacesetter potentials control and coordinate the frequency and direction of the contractions.

Electrical stimulation of the gastrointestinal tract has been proposed to treat motility related disorders and other gastrointestinal diseases. The electrical stimulation has been proposed in a number of forms, such as, e.g., pacing, electrical contractile stimulation or other stimulation, e.g., to treat nausea or obesity. Electrical pacing of the gastrointestinal tract is generally defined as a periodic electrical stimulation that captures and/or controls the frequency of the pacesetter potential or slow wave activity of the intestinal organ (including in a retrograde direction). Electrical contractile stimulation generally refers to stimulation that directly causes or results in muscular contraction associated with the gastrointestinal tract In some disease states, dysrhythmias of the gastric pacesetter potentials may be present. The result of the abnormal pacesetter potentials may be gastric retention of food. Electrical stimulation of gastric tissue has been proposed to induce peristalsis. Electrical stimulation has also been proposed to treat obesity by altering gastric motility, or by stimulating neural pathways. For example, one treatment method causes the stomach to retain food for a greater duration. Electrical stimulation has also been proposed to slow the gastric emptying to treat a disorder known as dumping syndrome where the stomach empties at an abnormally high rate into the small intestine causing various gastrointestinal disorders. In particular, electrical pacing of gastric pacesetter potentials has been proposed to induce regular rhythms for the pacesetter potentials with the intent of inducing regular or controlled gastric contractions.

Within the stomach, at least one pacemaker region has been identified near the interface of the fundus and the corpus along the greater curvature. This region has been one target for gastric pacing. Peristalsis controlled by this region is believed to serve to mix and break down food and propel small particles through the pylorus into the duodenum. It is believed that gastric emptying of liquids is also controlled by the fundus. This region is believed to create with characteristic contractions, a pressure gradient between the fundus pylorus and duodenum that relates to the rate of gastric emptying.

An early attempt at a gastric stimulation device included an electrode at the end of a nasogastric tube or catheter. The nasogastric tube was passed into the stomach transnasally. Electrical stimulation was applied using an external stimulator unit through the electrode on the end of the tube. The return electrode was placed on the abdomen. This device required a transnasal procedure whenever stimulation was required.

Other devices used to pace the stomach have generally been implanted by accessing the outside of the stomach through an opening in the abdomen, either through open surgery or laparoscopic surgery. Electrodes have been attached to the stomach wall with attached leads extending through the abdomen.

These procedures involve implanting a pacemaker device in a subcutaneous or sub-muscular pocket. The devices are anchored into the subcutaneous or sub-muscular pocket initially by a suture anchor and eventually by fibrous tissue ingrowth around the unit. The pacemaker device housing is typically constructed of a titanium or stainless steel material with connectors molded into an epoxy header. The devices are thin in one dimension so that they are less visible when implanted directly under the skin or muscle layer. Therefore, in order to accommodate the necessary battery capacity, the devices are widely shaped, e.g. round or kidney shaped the other two dimensions. The leads extend from the unit's epoxy header to a stimulation site remote from the pacemaker unit.

A gastrointestinal pacemaker having phased multi-point stimulation has been proposed with electrodes placed in multiple points around the GI tract including on the inner or outer surface of the stomach. As described, the device could be preprogrammed or include an implantable pacemaker detachably coupled to the multiple electrodes in their various locations, and including an electronic controller that may be programmed by using an external programmer to set stimulation parameters. The implantable pacemaker is located remote from the stimulation sites.

Some gastric stimulation procedures have proposed electrical stimulation in response to sensing electrical pulses within the stomach within a particular range. Additionally, a device has been proposed to sense electrical parameters to determine the fullness of an organ and the absence of muscular contraction, and to deliver electrical muscular contraction stimulation to the organ in response.

In general, the currently proposed gastric electrical stimulation procedures are relatively invasive and require accessing the stomach through the abdomen, e.g., in an open or a laparoscopic procedure. The units have relatively wide dimensions in one plane. Accordingly, it would be desirable to provide a less invasive procedure and device for electrically stimulating the stomach.

A machine that places a nylon tag has been proposed for attaching a "payload" to the inner wall of a stomach. The machine places the tag through the stomach wall and back into the stomach in a manner that causes folding and may cause tissue damage when the smooth muscle of the stomach wall contracts. It would be therefore be desirable to provide an attachment device for attaching a device within the stomach wall that minimizes device pull out forces, and that minimizes tissue damage when the smooth muscle of the stomach contracts, especially in electrically stimulating the smooth muscle of the stomach.

SUMMARY OF THE INVENTION

The present invention provides a device, system and method for diagnosing and treating gastric disorders. The present invention further provides a device, system and method for gastric electrical stimulation. Electrical stimulation is generally defined herein to mean any application of an electrical signal or of an electromagnetic field to tissue of the stomach for a therapeutic purpose. In one variation, the device is designed to facilitate or expedite mixing or breaking down of food matter or liquids in the stomach. In another variation, the device is designed to control, facilitate or expedite movement of food matter or liquids through the stomach and into the small intestine. In another variation, the device is designed to stimulate the stomach to delay passage of food from the stomach and into the small intestine. Other stimulation effects are also contemplated, including but not limited to using stimulation to treat nausea, obesity or pain symptoms. The stimulation may affect the smooth muscle contractions and/or nerves associated with the stomach.

The stimulating (or diagnostic) device of the present invention resides within the patient's stomach. A preferred device includes: at least one stimulating electrode in electrical contact with the stomach wall; an electronics unit containing the electronic circuitry of the device; and an attachment mechanism for attaching the device to the stomach wall. One or more stimulating electrodes may be secured to the wall of the stomach by the attachment device. One or more stimulating electrodes may also be located on the electronics unit. In a preferred embodiment, at least one stimulating electrode is embedded in the wall of the stomach. Preferably the stimulation is provided through at least one pair of bipolar electrodes. Alternatively a remote return electrode may be provided in a monopolar device.

The attachment device may be either integrally formed with the electronics unit or removably attachable to the electronics unit. The attachment device and electronics unit may be deployed in two steps: first by identifying a site for attachment and attaching the anchor and second by attaching the electronics unit. The electronics unit may be removable from the attachment device and or deployed electrodes so that the electronics unit may be replaced after time. The stimulating electrodes may be coupled to the attachment device and/or the electronics unit. The attachment device may include, e.g., a mechanical means such as a screw, suture, staple, clip or other anchor. The attachment device may include a release mechanism for easy endoscopic removal of the stimulating device from the stomach. In a preferred embodiment, the attachment device serves at least two functions: to hold the device in place as well as providing the stimulation or sensing. Thus, the preferred stimulation device is both mechanically and electrically coupled to the stomach. Another preferred embodiment may include a stimulation device secured to the stomach with flexible leads attached to the preferred stimulation site.

The stimulation device is constructed of size and shape such that it can be deployed through the mouth and esophagus with the aid of an endoscope. As such, the electronics unit is preferably of a generally cylindrical shape. The device components are constructed of materials that allow it to withstand and function in the highly acidic environment of the stomach for two or more years. (The pH in the stomach may be, at times, as low as 1.0). Such materials are relatively inert to the environment. An example of such materials are: suitable inert polymers, for example, materials from the Polyolefin family like HDPE (high density polyethylene), LLDPE (linear low density polyethylene), and UHMWPE (ultra high molecular weight polyethylene); fluoropolymer materials like PTFE™ (poly tetrafluoroethylene), FEP™ (fluorinated ethylene propylene) and others; polymethylpentene, and polysulphons; some elastomers such as thermoplastic polyurethanes and C-Flex type block copolymers that are stable in acidic environments. The electrodes are preferably made of corrosion resistant metals such as, e.g. Platinum, Gold, Tantalum, Titanium and corrosion resistant alloys or one or more of these metals. The electronics unit or shell may alternatively be constructed of one or more of these metals or alloys. Electrodes are preferably coupled to the electronic circuitry through sealed electrical contacts or through leads extending into the housing through molded corrosion resistant materials such as those described above.

A preferred system of the present invention includes an endoscopic delivery system for delivering the stimulator through the esophagus and into the stomach where it is attached the stomach wall. One embodiment of the system includes a flexible endoscope or endoscopic instrument, for locating a preferred site in the stomach for device attachment. In one embodiment, the endoscope or endoscopic instrument comprises electrodes that may be placed on the inside of the stomach wall to measure electrical activity or impedance, or to deliver test stimulation pulsed to identify optimal stimulation parameters or locations. The endoscope also provides one or more conduits through which tools for attaching the device are inserted. In one variation of the system an endoscope is used to implant a stimulating device having an anchor and a main body that is attached in situ to the attachment device or anchor. Preferably the anchor attaches the electrode of the device to the stomach wall and the main body includes the device electronics for providing the electrical stimulation through the electrodes. Alternatively the electrodes may be attached to the stomach wall separately from the anchor. The system includes an endoscopic instrument or instruments for first attaching the anchor and then coupling the main body or electronics unit to the anchor. The device and delivery system in a preferred embodiment includes a release mechanism in the stimulator unit so that it may be removably attached to an anchor or attachment device within the stomach so that the stimulator unit may be exchanged if desired. A preferred embodiment of the endoscopic system of the invention provides a device for engaging a release mechanism on the attachment device or on the stimulator unit for disengaging the stimulator from the attachment device or for disengaging the attachment device from the stomach wall.

In addition to the device being capable of stimulating the stomach wall, the electrodes of the device may also be used for diagnostic purposes. For example, the electrodes may be used to sense and observe electrical activity in the stomach wall. Such sensing may be used over time to identify patterns, diagnose diseases and evaluate effectiveness of various treatment protocols. For example irregular or lack of EMG activity may be sensed. Stimulation may be provided in response to sensed EMG activity or lack of activity.

In one variation, sensors can be included in the device or separately for sensing various parameters of the stomach. The sensors may be mounted on the electronics unit, an attachment mechanism, or by other means, for example, in an independently attached device for example attached with an anchor. The stimulation device may include a mechanical sensor that senses, for example, stomach wall contractions. As the stomach contracts, the stomach wall typically becomes thicker. In a preferred embodiment a device implanted in the stomach wall includes a strain gauge that is able to sense change in stomach wall thickness. Alternatively, electrical sensors may detect changes in impedance due to changes in wall thickness from smooth muscle contractions. Other examples of such sensors may include, for example, pH sensors, impedance sensors, pressure sensors and temperature measuring devices such as a thermocouple.

The stimulation device may be programmed to deliver stimulation in response to sensing electrical parameters or other sensed parameters. For example, a pH sensor may be used to determine when food has been ingested. When the pH changes in a manner, indicating food ingestion, the stimulation device may be instructed to deliver stimulation pulses to stimulate gastric motility. The device may also be user controlled, where the recipient of the device is able to externally activate the device, for example by using an external unit which delivers a control signal via telemetry. A temperature sensor may be used, for example, to determine when food has been ingested, by a change in temperature. The device may begin stimulating the stomach upon detecting sudden change in temperature. Pressure sensors may be used to sense motility patterns, e.g. presence, strength or frequency of contractions. Mean pressure shifts may be observed to identify fundal contractility. The stimulation device may also use sensed parameters to program or reprogram the device stimulation program. For example, measuring impedance changes through a circuit coupled to the electrodes (e.g., delivering a constant current or voltage across the electrodes to determine impedance) or determining the contractile behavior of the stomach using a strain gauge, in response to stimulation pulses, the effectiveness of the stimulation pulses may be monitored and adjusted to provide optimal response. The stimulation program may also include an automatic adjustment in response to changes in pressure measurement.

Other diagnostic or treatment devices may be attached to the inside of the stomach wall, for example using a separate or integrally formed anchoring device. Preferably such devices are introduced and attached to the stomach wall endoscopically. Such devices may include, for example, drug delivery devices, a gastric balloon, sensing or diagnostic devices. In one embodiment when excessive acid concentration is sensed using a pH sensor, a device is triggered to release an antacid drug, e.g., using a drug delivery pump.

The present invention also provides an attachment device for attaching a functional device to the stomach wall. The functional device may be a sensor for sensing various parameters of the stomach or stomach environment, or may be a therapeutic delivery device. The devices may be attached to the attachment device in a separate housing or may be integral with the attachment device. The functional devices may be powered by a battery included with the device or the functional devices may be inductively powered. In a preferred embodiment, the attachment device is attached such that the device does not substantially constrain the stomach in the plane of smooth muscle contractions and to minimize stresses in the tissue, to reduce the potential for tissue damage or device dislodgement. Preferably the attachment device attaches in a manner that avoids folding of the stomach wall. In one preferred embodiment, the attachment device is attached by piercing at least a portion of the stomach wall at a single point of penetration into the stomach wall. Also, in one embodiment the attachment device pierces the stomach wall in a direction perpendicular to the natural orientation of the stomach wall. Further, in a preferred embodiment, the attachment device extends through the stomach wall with a backing mechanism located external to the stomach wall. Preferably such backing mechanism is relatively atraumatic to the stomach outer wall and surrounding tissue and has a relatively high surface area in relation to the width of the attachment device or puncture hole. Another preferred embodiment provides an adjustable bumper holding the anchor to the inside of the stomach wall. Such bumper is also preferably designed to have a relatively high surface area and to be relatively atraumatic to the stomach wall. Another preferred embodiment provides an attachment device with a quick release mechanism that enables relatively easy endoscopic removal of the attachment device from the stomach.

Preferred embodiments of various aspects of the invention are described in the following detailed description.

DETAILED DESCRIPTION OF THE DRAWINGS

FIG. 7 is a side partial cross sectional view of the proximal end of an endoscope of the inventive system.

FIG. 8 is a side view of a distal end of the endoscope of the inventive system.

FIG. 9 is distal end view of the endoscope of FIGS. 7 and 8.

FIG. 12 illustrates a side elevational view of the main body of the stimulator of the first embodiment of the present invention.

FIG. 13 illustrates a side elevational view of the main body and anchor of the stimulator where a tether coupled to the anchor is threaded through an opening in the main body to guide the main body to the anchor.

FIG. 14 illustrates a partial cut away side elevational view of the stimulator of the first embodiment of the present invention attached to the stomach wall.

DETAILED DESCRIPTION OF THE PREFERRED EMBODIMENTS

Figure 1:
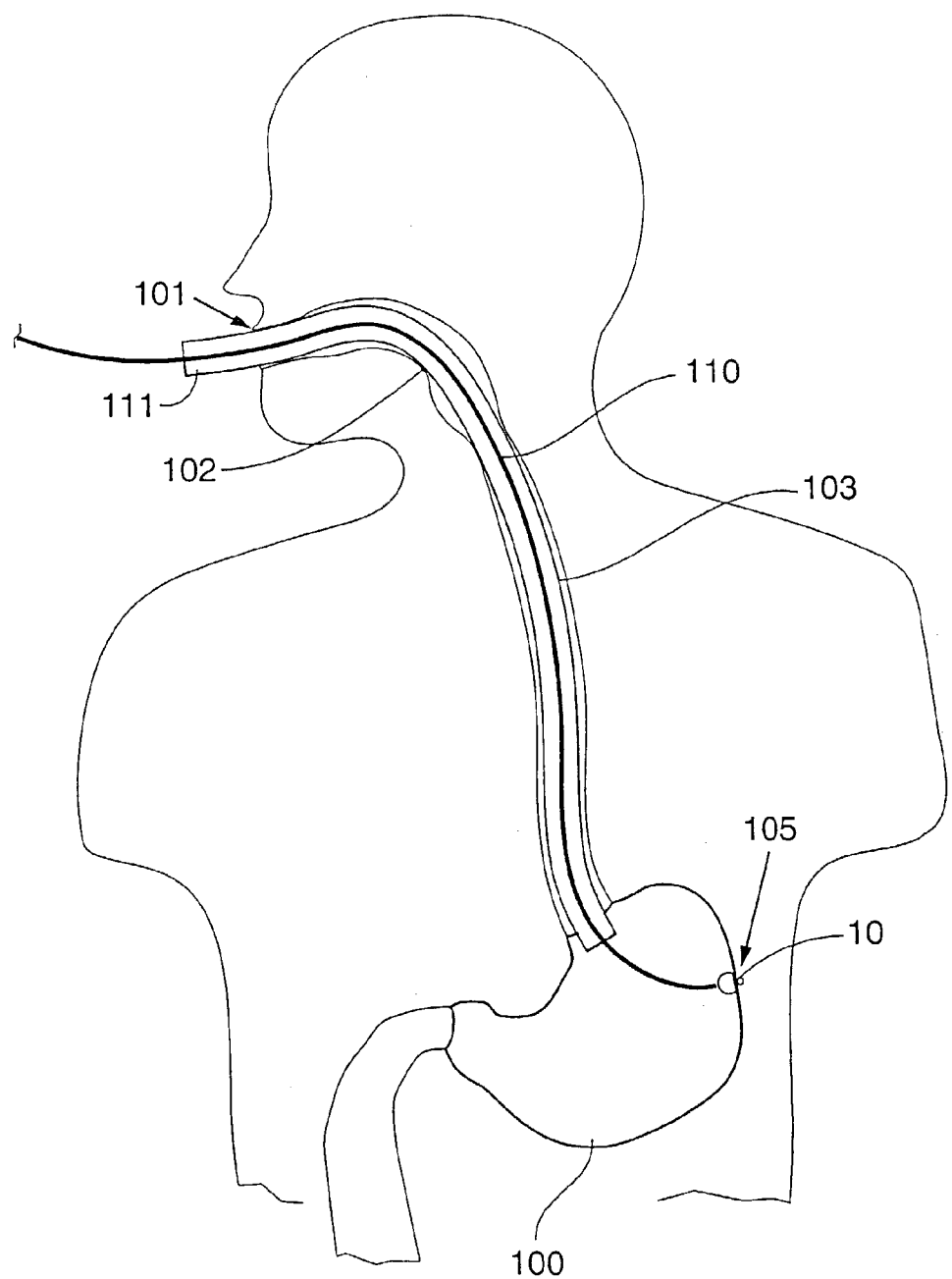
FIG. 1 is a partial cross sectional view of a system of a first embodiment of the present invention in use in placing an electric stimulator in a patient's stomach.

Referring to FIGS. 10-14 and 18-22, a stimulator 10 of a first embodiment is illustrated. The stimulator 10 comprises an anchor 123 and a main body portion 20. The anchor 123 comprises an elongate member 124 having and expandable distal end 125 and a stimulating electrode 126 in the form of a ring of a corrosion resistant metal conductor such as Platinum, Gold, Tantalum, Titanium or suitable alloys thereof, extending around the elongate member 124 just proximal of the expandable end 125. The anchor 123 may be constructed of a radiopaque material. Alternatively, the anchor 123 may include radiopaque markers located on the device so that the location and orientation of the device may be identified, particularly after it has been placed. At least a portion of the anchor 123 is preferably coated with an antibiotic material, such as gentamicin sulphate or a silver/silver salts coating, particularly in locations that it will extend through or come in contact with the stomach wall. A notch 127 extending around the elongate member 124 is located proximally of the stimulating electrode 126, for connecting the anchor 123 to the main body portion 20, containing the stimulator electronic circuitry 25. An electrical contact member 128 comprising a corrosion resistant metal ring extends circumferentially around the elongate member 124 proximal of the notch 127. The electrode 126 and the contact 128 are electrically coupled through a wire 129 or other conductor extending through the elongate member 124. The proximal end of the anchor 123 has an opening 130. A tether 131 is secured to the opening 130. The tether 131 is used to guide the main body portion 20 into place. The tether 131 is also used to pull on the anchor 123 while the main body portion is pushed into place both to provide a guide and to hold the anchor 123 in place.

A strain gauge 121 is located on the elongate member 124 of the anchor 123. The strain gauge 121 is coupled through conductors 121a and 121b to electrical contacts 128a, 128b respectively. Electrical contacts 128a and 128b are constructed and sealed when coupled to the main body 20, in a manner similar to contact 128.

The main body portion 20 comprises a sealed housing 21 including electronic circuitry 25. The electronic circuitry 25 provides sensing, stimulating electronic pulses through the electrodes to the stomach wall, and telemetry communication with an external unit such as a reader, recorder or controller. The housing 21 includes an outer shell having a distal face 26 for interfacing with the stomach wall. The main body 20 also includes a radiopaque marker 31, preferably a radiopaque stimulator serial number (e.g., sprayed onto a location in the housing 21) so that the device and its location may be identified. The outer shell is constructed of an acid corrosion resistant material such as a suitable inert polymer, for example, materials from the Polyolefin family like HDPE (high density polyethylene), LLDPE (linear low density polyethylene), and UHMWPE (ultra high molecular weight polyethylene); fluoropolymer materials like PTFE™ (poly tetrafluoroethylene), FEP™ (fluorinated ethylene propylene) and others; polymethylpentene, and polysulphons; some elastomers such as thermoplastic polyurethanes and C-Flex type block copolymers that are stable in acidic environments. Additionally the outer shell may be constructed of an acid corrosion resistant metal such as Platinum, Gold, Tantalum, Titanium, or suitable alloys thereof. The distal face 26 is preferably coated with an antibiotic material, such as gentamicin or silver/silver salts coating. The main body 20 further comprises an electrode 32 located on the distal face. The electrode 32 is constructed of an acid corrosion resistant material such as Platinum, Gold, Tantalum, Titanium, or any suitable alloys thereof.

Figure 22:
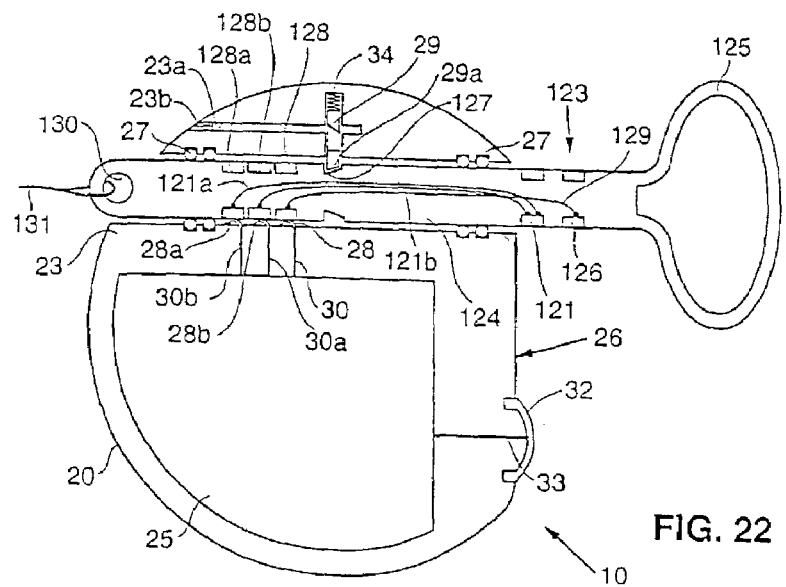
FIG. 22 illustrates a side cross sectional view of the main body and anchor of the first embodiment locked together.

The main body portion 20 further comprises a channel 23 through which the tether 131 is threaded for alignment with the anchor 123 (FIG. 13) and for receiving the elongate member 124 of the anchor 123 (FIGS. 14 and 22). A second channel 23a extends parallel to the channel 23 from an opening in the proximal side of the main body 20 and ending within the main body 20. The second channel 23a is for receiving a connect/release tool 38 described in more detail below.

The channel 23 includes an opening 24 in the distal face 26 of the body portion 20 as well as an opening 22a in the proximal side 22 of the main body 20. The walls of the channel 23 include a plurality of acid resistant elastomeric seals 27 formed of a material such as, for example, polyurethanes, rubbers or C-Flex type block copolymers. In between the seals 27 is a flexible electrical contact 28 for contacting the electrical contact 128 of the anchor 123 and a latch 29 for engaging the notch 127 of the anchor 123. Thus, the electrical contact 28 will be located in a sealed area of the channel 23, between seals 27, protecting it from the highly acidic environment of the stomach. The seals 27 also act as electrical insulators that prevent unintended current pathways between the electrical contact 28 and the electrode 32. The electrical contact 28 is coupled to the electronic circuitry 25 of the main body portion 20 through a conductor 30 extending from the circuitry 25 through the housing 21 to the contact 28. The second stimulating electrode 32 located on the distal face 26 of the main body 20 is coupled to the electronic circuitry 25 by way of a conductor 33. As an alternative to being coupled to the electronic circuitry through a sealed contact, the electrode 126 may be constructed in a manner similar to electrode 32 using a corrosion resistant material that is directly coupled to the electronic circuitry (for example, where the anchor is integrally formed with the stimulator 10 or where the electrode 26 is located on the housing).

As illustrated in FIG. 22, when the main body portion 20 and the anchor 123 are connected, the elongate member 124 of the anchor 123 extends into the channel 23 so that the notch 127 and the electrical contact 128 are located between seals 27. The electrical contacts 128, 128a, and 128b are in contact with flexible electrical contacts 28, 28a, and 28b respectively, and the latch 29 is located within the notch 127 so that the elongate member 124 of the anchor 123 is fixed within the main body portion 20.

Figure 21:
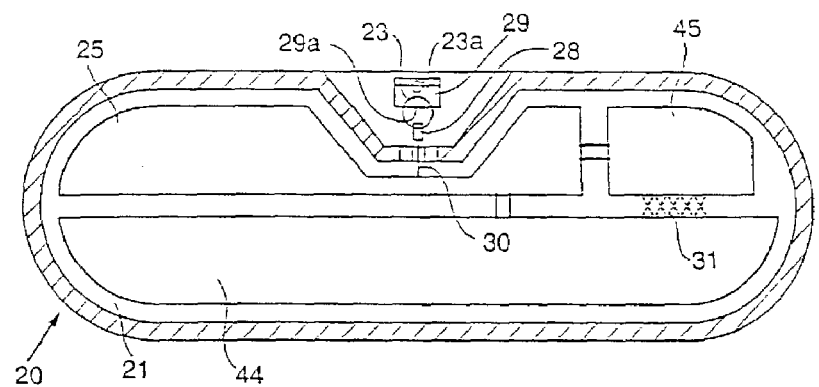
FIG. 21 illustrates an end cross sectional view of the main body illustrated in FIG. 12 with a quick connect in a closed, locked position.
Figure 19:
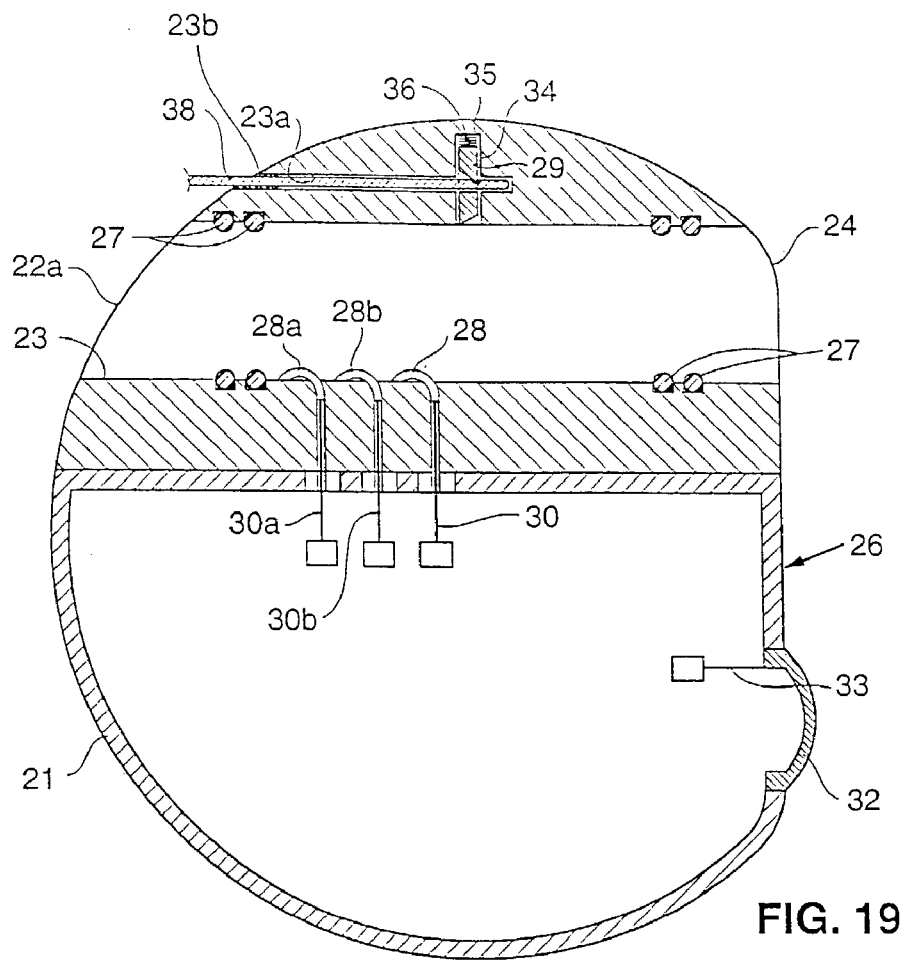
FIG. 19 illustrates a side cross sectional view of the main body illustrated in FIG. 12.
Figure 19A:
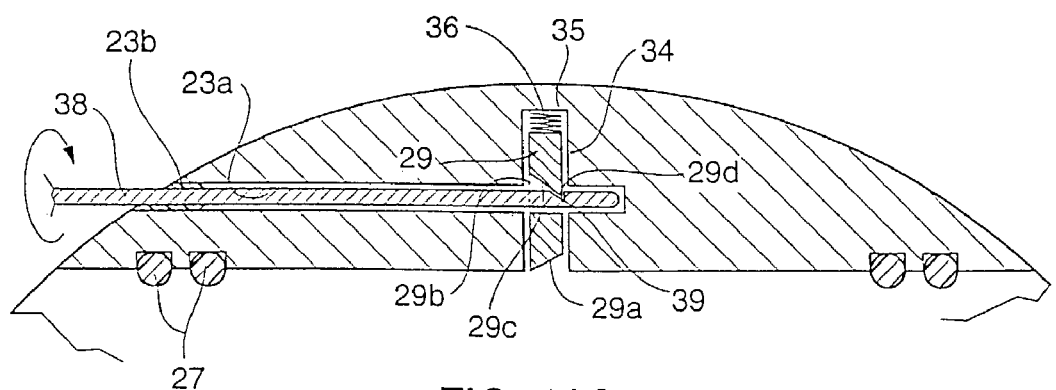
FIG. 19A illustrates an enlarged view of the latch mechanism of the main body portion shown in FIG. 19 with the latch in a closed position.
Figure 20:
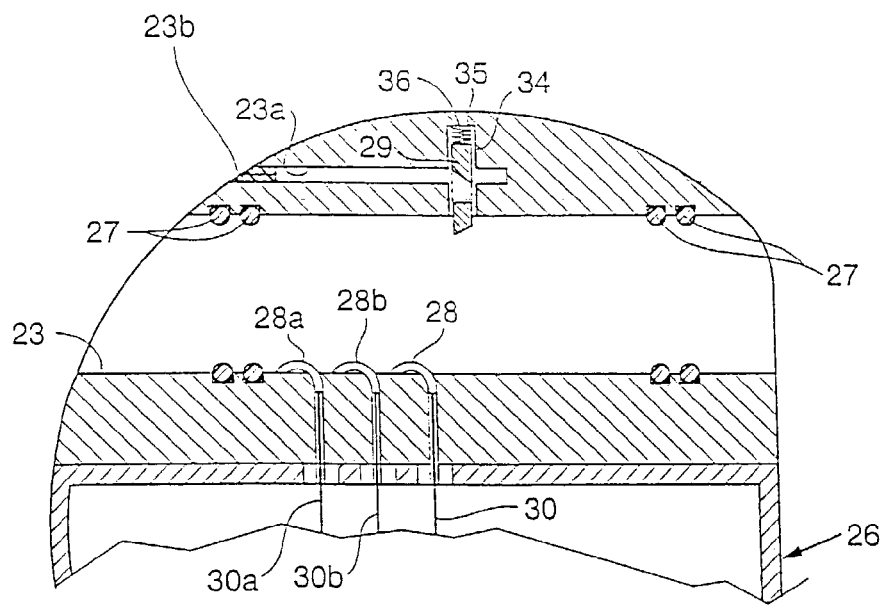
FIG. 20 illustrates an end cross sectional view of the main body illustrated in FIG. 12 with a quick connect in an open, unlocked position.
Figure 20A:
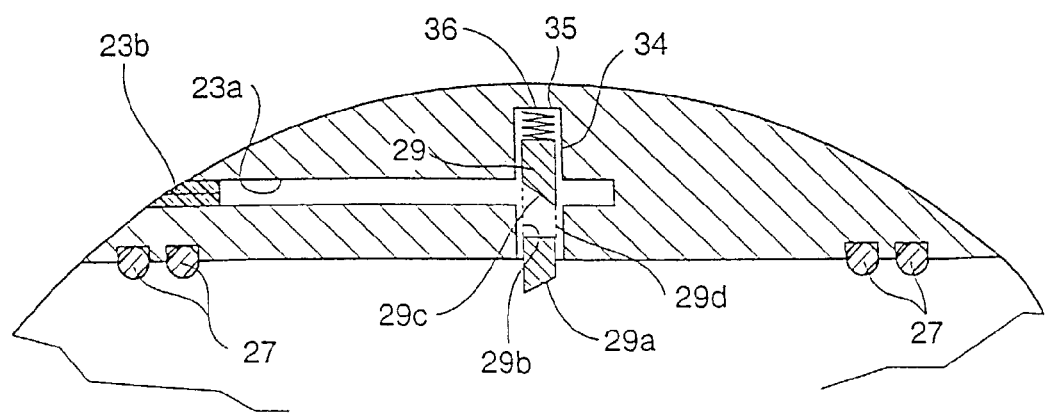
FIG. 20A illustrates an enlarged view of the latch mechanism of the main body portion shown in FIG. 20 with the latch in an open position.

FIGS. 19-21 show the latch mechanism 29 in the main body 20 that is used to connect the main body 20 to the anchor 123. The latch 29 is located within a closed channel 34 in the main body 20 that is oriented perpendicular to the channels 23 and 23a. A spring member 36 is located at the end 35 of the closed channel 34 between the end 35 and the latch 29. The spring 36 biases the latch 29 in a closed position as illustrated in FIG. 20 and described below. The latch 29 comprises a connecting end 29a that extends into the channel 23 when the latch 29 is in its closed position. The latch 29 further comprises an opening 29b formed in part by a cam surface 29c ending in tip 29d. When the latch 29 is in an open position (FIG. 19), the spring 36 is compressed and the cam surface 29a and the tip 29d are recessed into the closed channel 34. When the spring 36 is released, the latch 29 moves into the closed position where the cam surface 29a extends into the channel 23 and the cam surface 29c and tip 29d extend into the channel 23a.

In use, the latch 29 tends toward the closed position. In order to connect the anchor 123 with the main body 20, a connecting tool 38 is inserted into the channel 23a and the tool 38 engages the cam surface 29c to move the latch 29 into the open position. Channel 23a includes an elastomeric, self-sealing plug 23b with a slit for receiving the connecting tool 38. The plug 23b seals the opening in the channel 23a from external fluids, etc. The tool 38 includes a notch 39 in its distal end. The tool 38 may be locked into position in the channel 23a by rotating the tool so that the tip 29d of the cam surface 29c engages the notch 39. This prevents removal of the tool 38 from the channel 23a. Thus the tool 38 may be temporarily locked in the channel 23a with the latch 29 in an open position for insertion of the anchor 123 into the channel 23. The tool 38 may be released when the anchor 123 is in place, by rotating the tool so that the tip 29d of the latch 29 no longer engages the notch 39 in the tool 38. When connected, the elongate member 124 of the anchor 123 is located in the channel 23 and the latch connector 29a extends into the notch 137 in the elongate member 124, thereby connecting the anchor 123 and the main body portion 20. Alternatively, the main body portion 20 may be connected to the anchor 123 without the use of such a tool. In this case, the anchor 123 causes the latch to retract as the anchor 123 is inserted until the connecting end 29a of the spring-loaded latch 29 locks into place in the notch 137.

The tool 38 may be used in a similar manner as described above, to remove the main body 20 from the anchor 123, for example to replace the main body 20 or remove the stimulator 10. The tool 38 is preferably a device that may be inserted through a lumen in an endoscope. In such case, the tool 38 may first be placed through the endoscope and attached to the stimulator distal of the endoscope's distal end. This would particularly be the case where the stimulator is larger than the channels in the endoscope. Other endoscopic tools may be used to deploy or remove the stimulator 10 or main body 20. For example, a grasping tool may be used manipulate the device where the grasping tool has an actuator handle extending out of the proximal end of the endoscope. Also a magnetic tool may be used to engage and manipulate the stimulator during insertion or removal. A magnetic docking system may be used as well, to locate or orient the main body 20 in an aligned position with respect to the anchor 123. The main body, anchor insertion tool or endoscope may have magnets that provide for aligned connection between the main body 20 and anchor 123.

FIGS. 1-9 and 15-17 illustrate an endoscope of the system of the present invention and the placement of the electrical stimulator 10 using the endoscope and associated instruments. FIG. 1 illustrates a flexible endoscope 110 such as, for example, of a type that used by gastroenterologists in treating the upper gastrointestinal tract. The endoscope 110 is used to locate an attachment site in the stomach 100 and attach the stimulator device 10 to the stomach wall of a patient. The flexible endoscope is of the type that is typically used by gastroenterologists in accessing the esophagus or stomach. The endoscope allows the physician to visualize while performing procedures on the upper gastrointestinal tract. The flexible endoscope may be, for example, a flexible fiber optic endoscope utilizing optic fibers for imaging or a video endoscope that uses a CCD (charge coupled device) to provide video images. Such endoscopes typically include a fiber optic light guide and a complex objective lens at the distal end to focus the image.

As illustrated in FIGS. 7-9, the endoscope comprises an elongate tube having a proximal handle portion 106 and a distal portion 115. The endoscope includes an aspiration channel 112 and irrigation/air channel 113. A fiber optic light source 93 for illuminating the stomach site extends through a fiber optic channel. A video lens 94 is located at the distal end of the endoscope, for receiving and focusing the image that is transmitted back through a channel in the endoscope 110. Corresponding light source input 95, video output 96, irrigation port 97, aspiration port 98 and auxiliary port 99, are located on the proximal handle portion 106. Knobs 107 and 108 are coupled at the proximal handle 106 for left/right and up/down steering mechanisms, respectively, that are used to steer the distal portion of the endoscope in a manner that is generally known to one of ordinary skill in the art. The endoscope 110 further includes an auxiliary channel 114 extending through the endoscope 110 and providing an opening through which surgical instruments may extend to reach the site 105. An additional auxiliary port may be provided for additional instruments or alternatively, the aspiration channel 112 may be used for additional tools if not otherwise required in a procedure. The distal portion 115 of the endoscope 110 includes an open distal tube 116, the end of which is placed against the stomach wall at the site 105. The distal tube 116 provides a space for stomach tissue to enter and be held in place when a vacuum pressure is applied.

Figure 2:
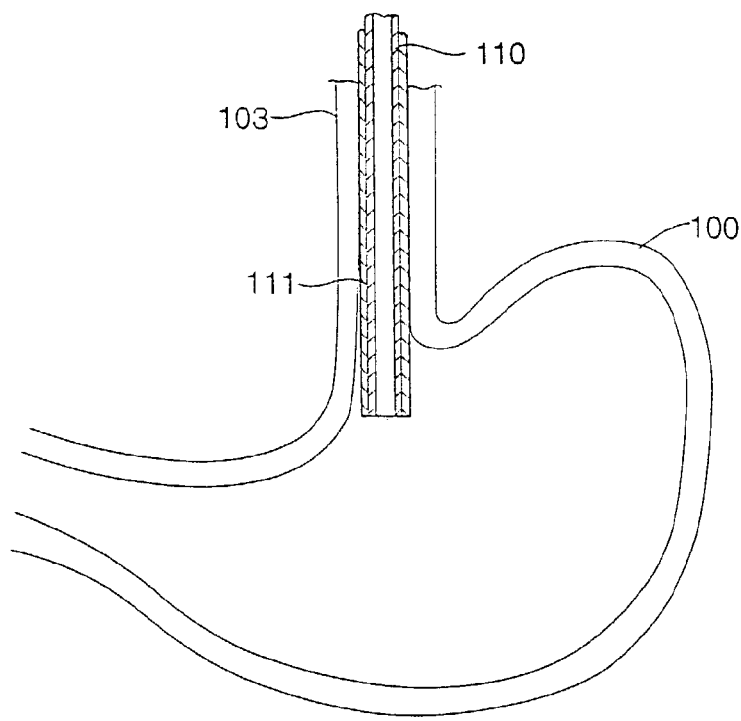
FIG. 2 is a partial cross section view, illustrating placement of an overtube in the first embodiment of the system of the present invention.

During the procedure the patient is given a numbing agent that helps to prevent gagging. As shown in FIG. 2 a protective overtube 111 with the endoscope 110 is passed through the mouth 101, pharynx 102, into the esophagus 103 and opening into the stomach 100. The overtube 111 is used to protect the esophagus, which may become irritated with repeated insertion and removal of instruments. The overtube 111 also helps prevent instruments and devices from inadvertently dropping into the trachea. In addition, the overtube 111 serves to protect the tools from the bacteria in the mouth and esophagus so that such bacteria are not passed on to the stomach wall. As illustrated in FIG. 9, the overtube 111a may also include additional channels 111a and 111b for inserting additional instruments.

Figure 3:
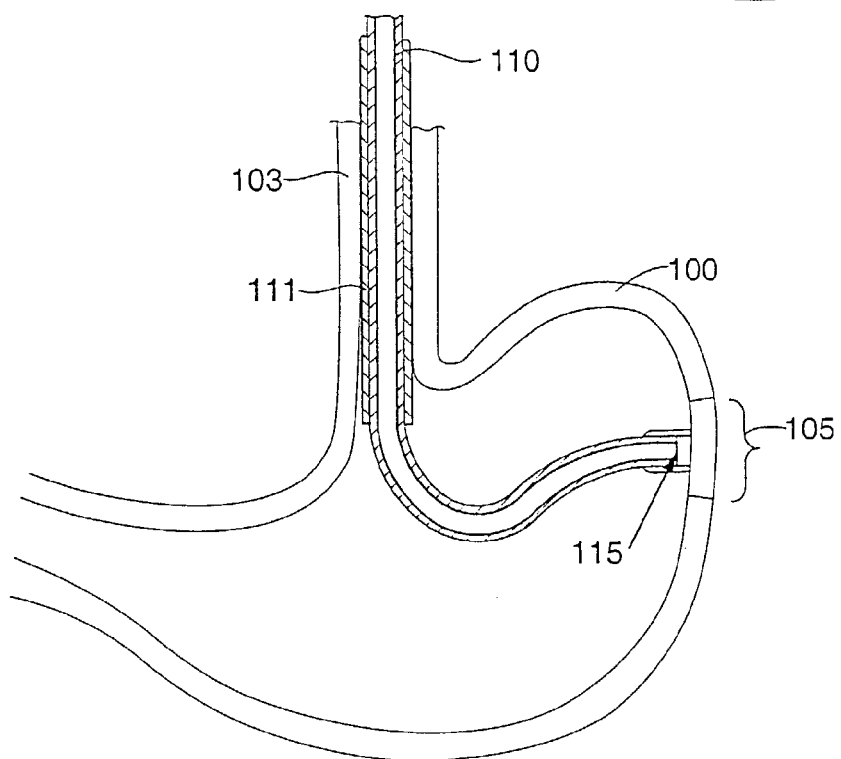
FIG. 3 is a partial cross sectional view of the placement of an anchor in the stomach in the first embodiment of the system of the present invention.

Preferably the instruments inserted into the patient's stomach are coated with an antibacterial material, in particular, the instruments that are used to pierce or otherwise come in contact with the stomach wall. As illustrated in FIG. 3, the endoscope 110 is extended distally out of the overtube 111 and is used to locate a site 105 on the stomach 100 for attaching the stimulator 10. Additionally or alternatively, an endoscope or a tool inserted through the esophagus may be used to detect intrinsic gastric electrical activity to help pinpoint the optimal site for a stimulator and/or electrode attachment to the stomach wall (See for example, FIGS. 35A and 35B and the corresponding description herein). In such a case sensing electrodes are coupled to the distal end of the endoscope or tool, with conductors extend out of the endoscope or patient's esophagus to a unit having a controller for receiving sensed electrical activity and identifying a surgical site for stimulator attachment.

Figure 4:
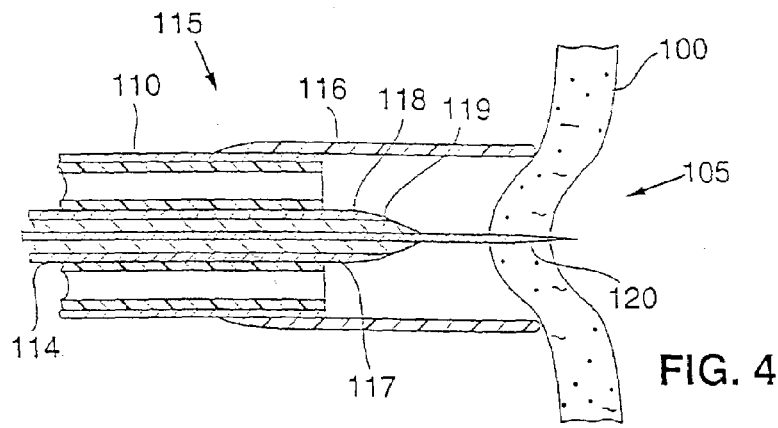
FIGS. 4-6 are detailed partial cross sectional views illustrating the placement of the anchor in the first embodiment.
Figure 5:
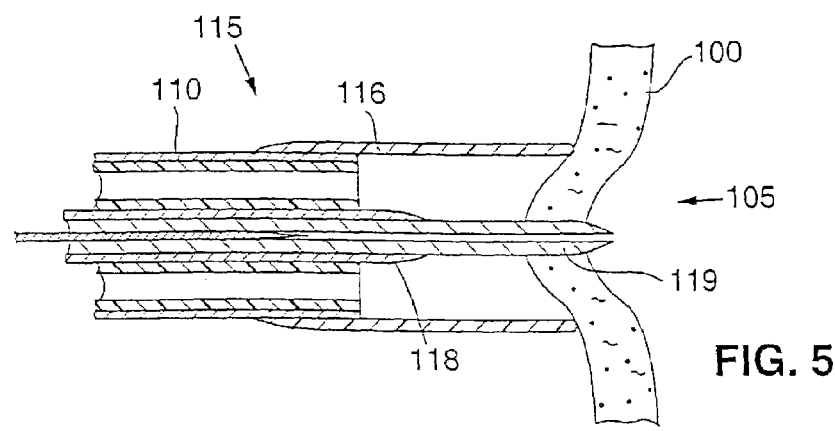
Figure 6:
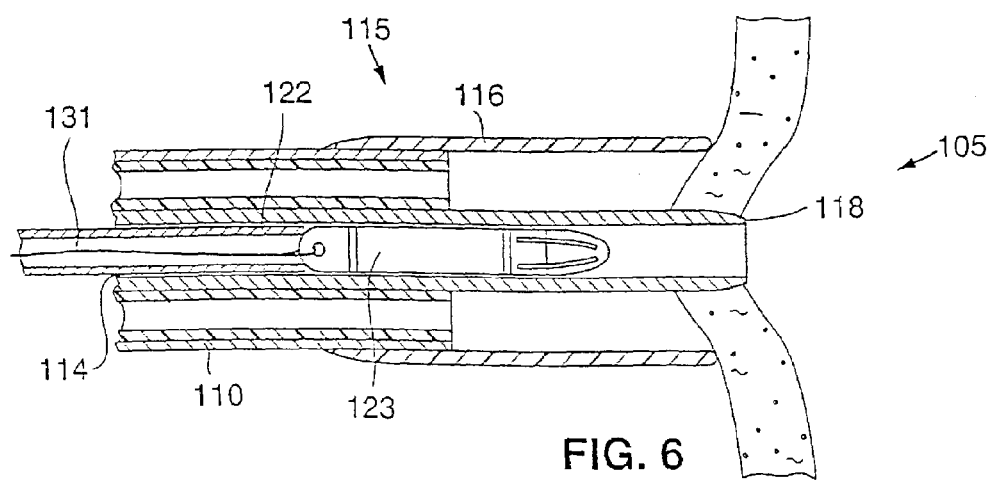

As shown in FIGS. 4-6 an introducer 117 is inserted through the auxiliary channel 114. The introducer 117 comprises an outer cannula 118, a dilator 119 extending through the cannula 118, and a needle 120 extending through the dilator 119. Each of the cannula, 118, dilator 119 and needle 120 are separately actuable at the proximal end in a manner that would be apparent to one of ordinary skill in the art, for example, in a manner similar to such devices utilized in catheter introducer sets. After the open distal tube 116 is located at a site 105 in the stomach 100, a vacuum pressure is applied through the aspiration channel 112 to engage, stabilize and hold the tissue at the site 105. As illustrated in FIG. 4, the needle 120 is advanced distally through the tissue of the stomach wall. As illustrated in FIG. 5, the dilator 119 is then advanced over the needle 120 through the stomach wall. The needle 120 is then retracted proximally out of the dilator 119 and is removed from the endoscope 110. The cannula 118 is advanced over the dilator 119 and the dilator 119 is removed proximally from the endoscope 110.

Figure 10:
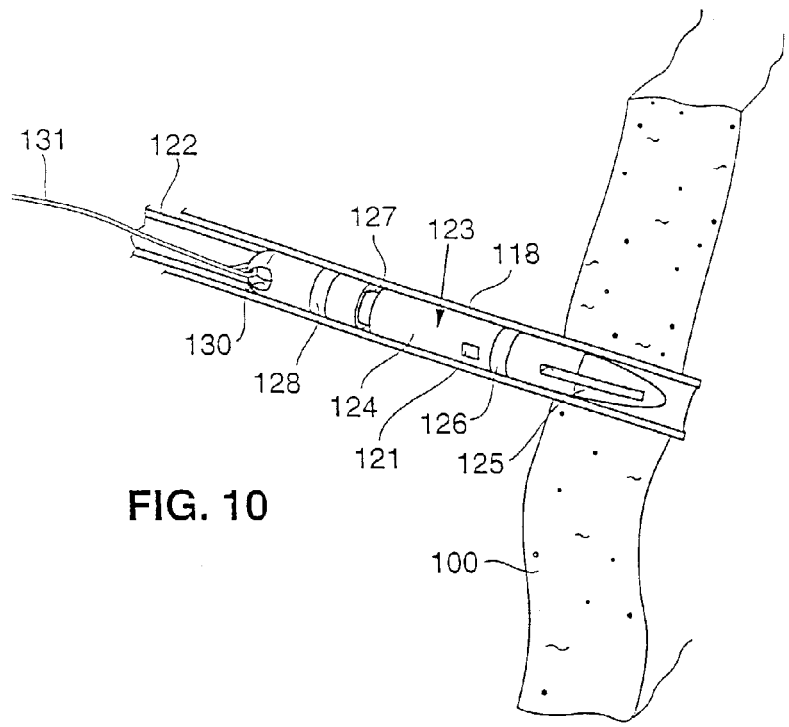
FIG. 10 illustrates a partial cut away side elevational view of an anchor of the first embodiment initially placed in the stomach wall

As illustrated in FIG. 6, with the cannula 118 through the stomach wall, the anchor 123 may be placed into the cannula 118 from the proximal end of the endoscope. Using a push tube 122 having a diameter that is small enough to fit within the cannula 118, placed proximally of the anchor 123, the anchor 123 is distally advanced through the cannula 118 located within the stomach wall (FIG. 10).

Figure 11:
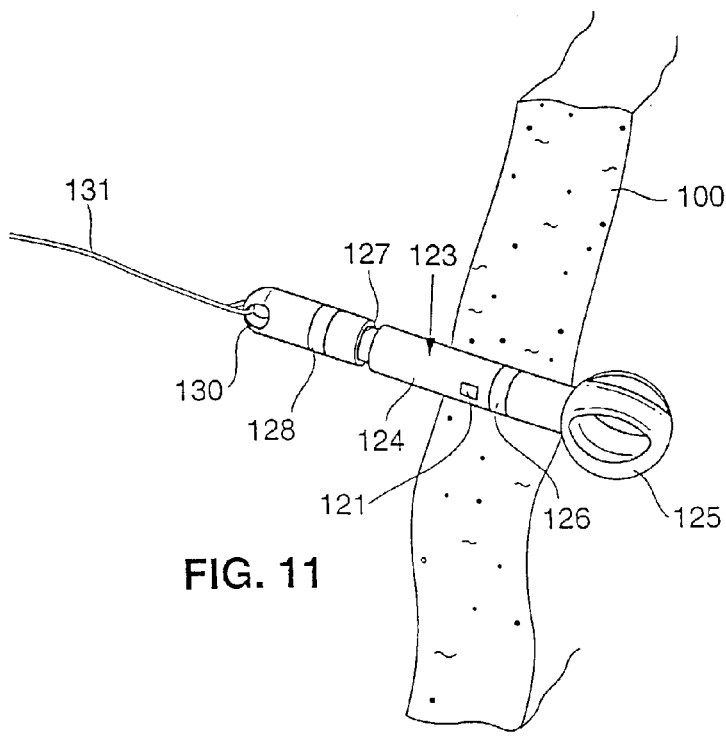
FIG. 11 illustrates a partial cut away side elevational view of a fully deployed anchor of FIG. 10.

The push tube 122 pushes the anchor 123 through the cannula 118 until the expandable distal end 125 extends out of the stomach wall in the peritoneal cavity. (FIG. 11) Before insertion, a tether 131 is secured to the opening 130 and extends through the push tube 122 out of the proximal end of the endoscope 110. The expandable distal end 125 is formed of an elastic or spring material that tends to spring open into its expanded shape when the distal end 125 is no longer constrained by the cannula 118. (FIG. 11). Once the anchor 123 is in place, the cannula 118 is withdrawn from the endoscope 110 and the endoscope 110 may also be removed from the over tube 111 leaving the tether 131 in place extending from the anchor 123 out of through the over tube 111 and out of the patient's mouth 101. The tether 131 is to be used to guide the main body 20 of the stomach to the anchor 123. The tether 131 may comprise a thread or suture-like device or may be a thin flexible guide wire like device. The tether 131 may be tied or otherwise anchored to hole 130 in anchor 123 or it may be looped through hole 130 in anchor 123 such that two strands lie parallel to each other in the overtube 111 and pass out of the patient's mouth.

Figure 15:
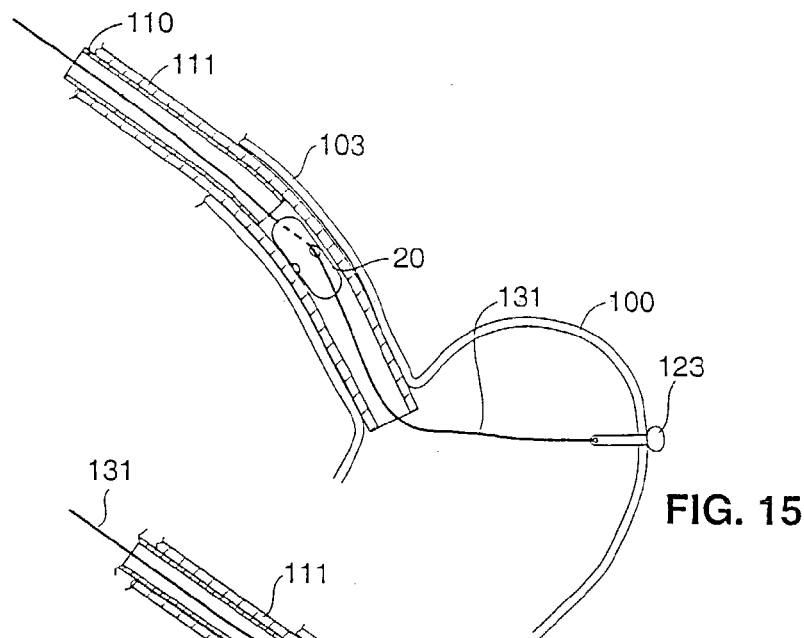
FIGS. 15-17 illustrate respectively the main body of the first embodiment of the stimulator as it is placed through the esophagus, into the stomach and connected with the anchor.
Figure 16:
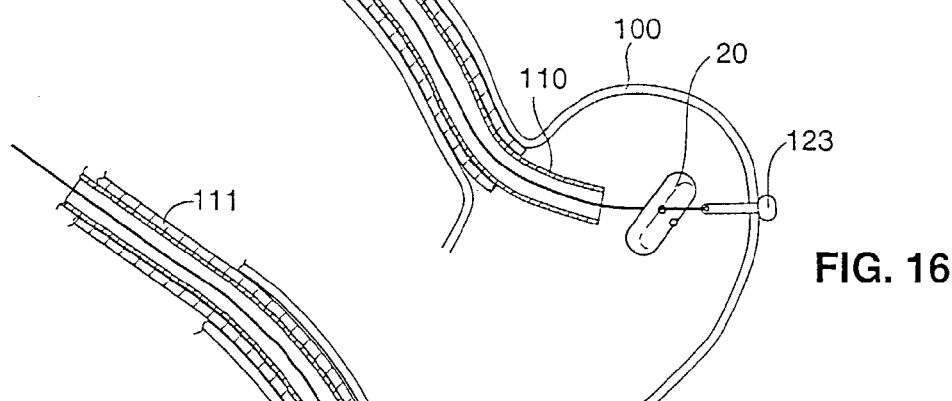
Figure 17:
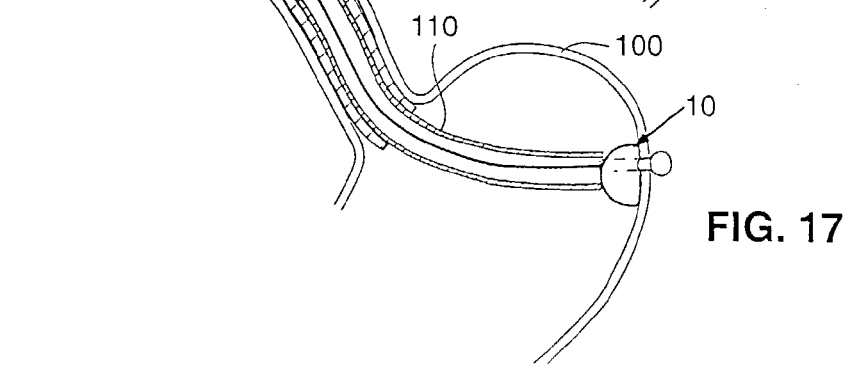
Figure 18:
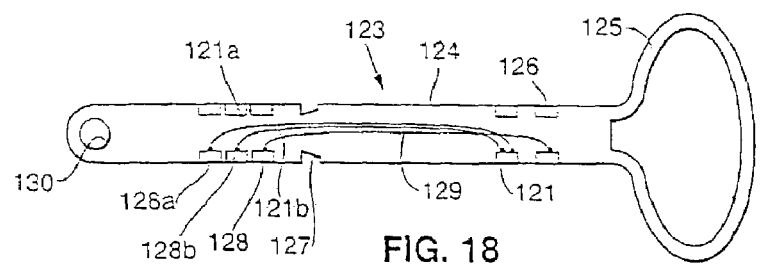
FIG. 18 illustrates a side cross sectional view of the deployed anchor of FIG. 11.

FIGS. 15-17 illustrate a preferred procedure for connecting the main body portion 20 of the stimulator 10 to the anchor 123 in place in the stomach wall. The main body 20 is threaded on to the tether 131 that is attached to the anchor 123 through the channel 23 in the main body 20. The tether 131 which extends through the over tube 111, guides the channel 23 to the elongate member 124 of the anchor 123 for attachment. The threaded main body portion 20 is preferably placed within the over tube 111 with the endoscope 110 located proximal of the main body portion 20 within the overtube 111. The tether 131 is also preferably threaded through the overtube 111, placed in parallel with the endoscope 110 through the overtube 111 or one of its channels 111a, 111b. The tether may be placed in a lumen extending through the endoscope 110. Tool 38 extends through the auxiliary channel 114 and is coupled distally of the distal end 115 of the endoscope, to the main body 20 through the channel 23a. The endoscope 110 distal portion 115 also engages the main body portion 20 and provides a force to move the main body portion 20 through the over tube 111. (FIG. 15). The endoscope 110 further provides visualization of the coupling process. The tool 38 and tether 131 together further locate the main body portion 20 with the anchor 123 as it extends through the stomach 100 to the site 105. (FIG. 16). Finally, the tool 38 provides additional force to attach the main body portion to the anchor 123 (FIG. 17). The tool 38 is then removed from the channel 23a in the main body 20 and out of the endoscope's proximal end. Alternatively the main body 20 may be placed in position, coupled to the anchor 123 by using the tether 131 and the distal portion 115 of the endoscope to guide the main body 20 into place. (See e.g., FIGS. 15-17). In an alternative embodiment, a magnetic docking system is used wherein the distal end 115 of the endoscope 110, main body 20, and/or anchor 123 includes a magnet and/or corresponding metal used to align and position the anchor 123 and main body 20 with respect to each other.

After the main body portion 20 has successfully been coupled to the anchor 123, an endoscopic scissor or other cutting device may be provided through the auxiliary channel 114 in the endoscope 110 to cut the tether 131. As illustrated in FIG. 14, when the stimulator is attached to the stomach wall, the stimulating electrode 32 is located within the tissue of the stomach wall, providing electrical contact. While the second stimulating electrode 32 on the distal face 26 interfacing with the stomach 100, is in electrical contact with the inner surface 100b of the stomach wall.

Figure 23:
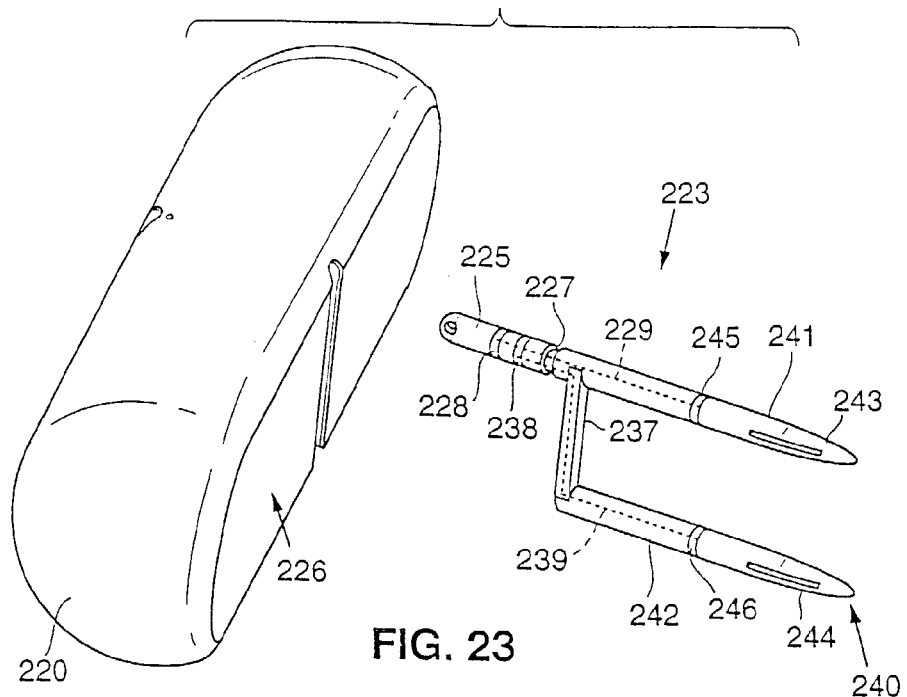
FIG. 23 illustrates a side elevational view of the anchor and main body of a second embodiment of the stimulator of the present invention.
Figure 24:
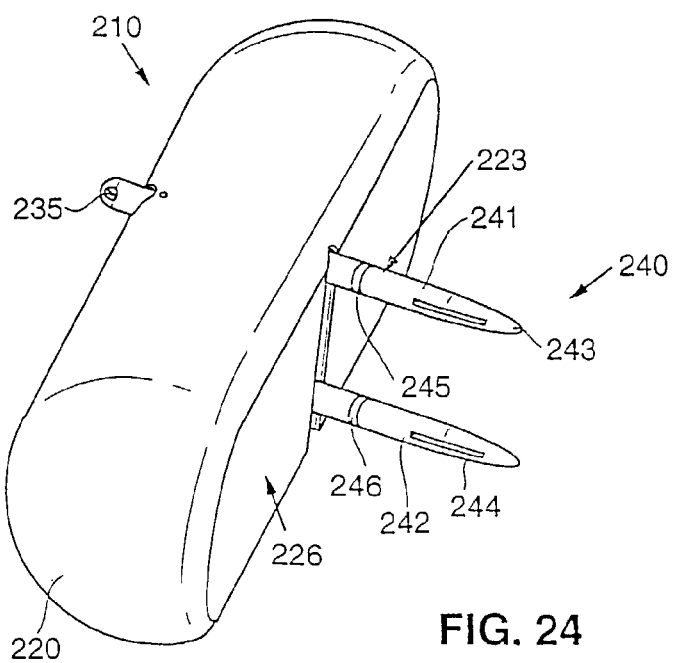
FIG. 24 illustrates a side elevational view of the embodiment of FIG. 23 with the anchor and main body attached.

FIGS. 23 and 24 illustrate a second embodiment of the stimulator of the present invention. Stimulator 210 comprises a main body portion 220 and an anchor 223. The anchor 223 comprises an elongate proximal member 225. The elongate proximal member 225 includes a tether opening 235 in the proximal end, electrical contacts 228, 238, and a notch 227 for connecting the main body portion 220 to the anchor 223. The distal portion 240 of the anchor 223 comprises two prongs 241, 242. Prongs 241, 242 have expandable distal ends 243, 244 respectively that are constructed in a similar manner as the expandable distal end 125 described above with respect to the first preferred embodiment. A stimulating electrode 245 is located on prong 241 and an electrically opposite second stimulating electrode 246 is located on prong 242. Stimulating electrode 245 and second stimulating electrode 246 are coupled to electrical contacts 228 and 238 respectively by conductors 229 and 239 extending through prongs 241, 242 respectively into the elongate proximal member 225. Prongs 241 and 242 are connected by a spacer 237.

Main body portion 220 includes a channel 215 with an opening 216 on the distal face 226. The channel 215 and the opening 216 on the distal face have shapes that allow them to respectively receive the elongate proximal member 225 and the spacer 237, thereby sealing the opening 216. The electrical contacts 228, 238 to the anchor 223 are coupled to electrical contacts within the channel 215 of the main body portion 220 in a manner similar to the coupling of contacts 128, 128a and 128b of anchor 123 and contacts 28, 28a, and 28b of main body portion 20 described with reference to the first embodiment herein. Also the notch 227 engages a latch similar to the latch 29 described above. The notch 227 and latch and the electrical contacts 228, 238 are isolated from the acidic environment of the stomach using seals such as the seals 27 described above with respect to the first embodiment. Alternatively, the electrodes 245, 246 may be constructed in a manner similar to electrode 32 using a corrosion resistant material that is directly coupled to the electronic circuitry (for example, where the anchor is integrally formed with the stimulator or where one or more of the electrodes 245, 246 are located on the main body portion).

The anchor prongs 241, 242 may be deployed in a similar manner as anchor 123 is deployed, using a dual needle introducer or, alternatively by deploying each prong 241, 242 independently and later connecting the prongs 241, 242 with the spacer 237.

Figure 36A:
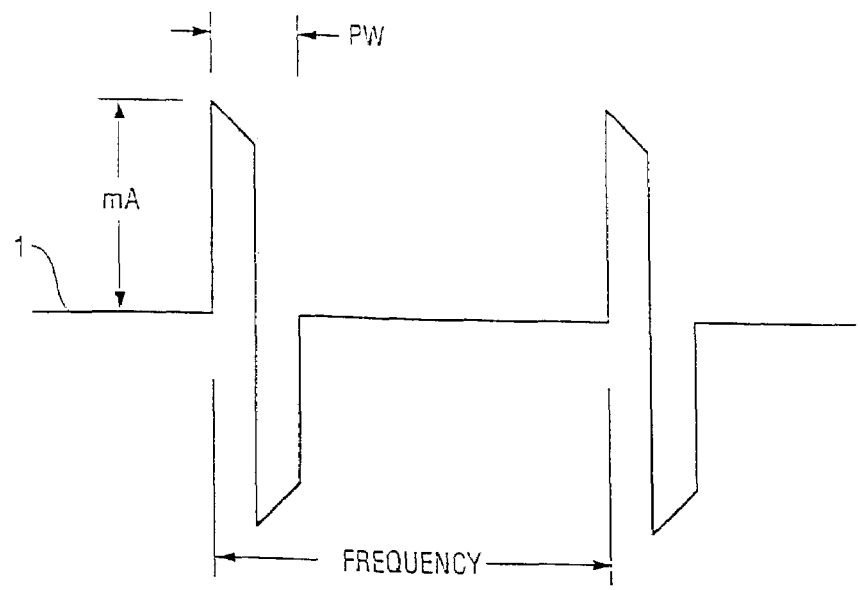
FIGS. 36A and 36B illustrate exemplary stimulation waveforms.
Figure 36B:
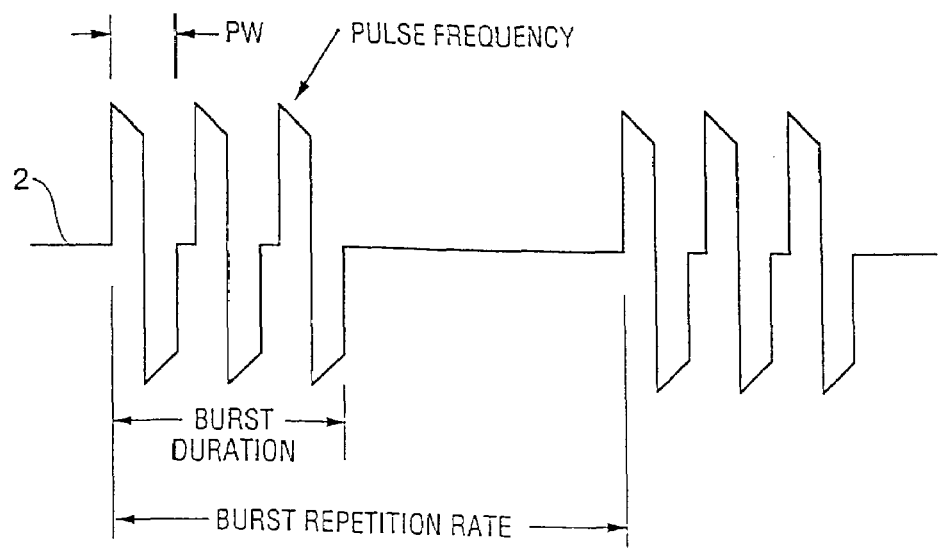

In use, once the stimulator (e.g., 10, 210, 310 or 380) is deployed, electrical stimulation is provided through electronic circuitry 25. The electronic circuitry 25 is capable of producing various types of programmable waveforms. FIGS. 36A and 36B illustrate examples of stimulation waveforms that may be used in stimulating the smooth muscle lining of the intestinal tract. FIG. 36A illustrates a waveform design for stimulating the intestinal tract at a pacing rate. In a preferred embodiment, the waveform 1 has a pulse amplitude of between 0.5 and 20 milliamps, a pulse width of between 0.5 and 10 milliseconds, and a frequency of about between 1 and 5 pulses per minute. FIG. 36B illustrates an alternative waveform design for stimulating the intestinal tract. The waveform 2 utilizes bursts of pulses rather than a single pulse with a burst repetition rate to be selected, preferably of about 3 cycles per minute. The duration of a burst in this example is about 100 ms and an amplitude of about 10 mA. In this example, the frequency of the burst pulses during a burst is between about 50 to 100 Hz, and as is well known to those skilled in the art, there are many different types of electrical stimulation programs and strategies which can be utilized for providing electrical stimulation parameters through the circuitry 25, the principal focus being providing electrically stimulating parameters for the stomach.

Figure 25:
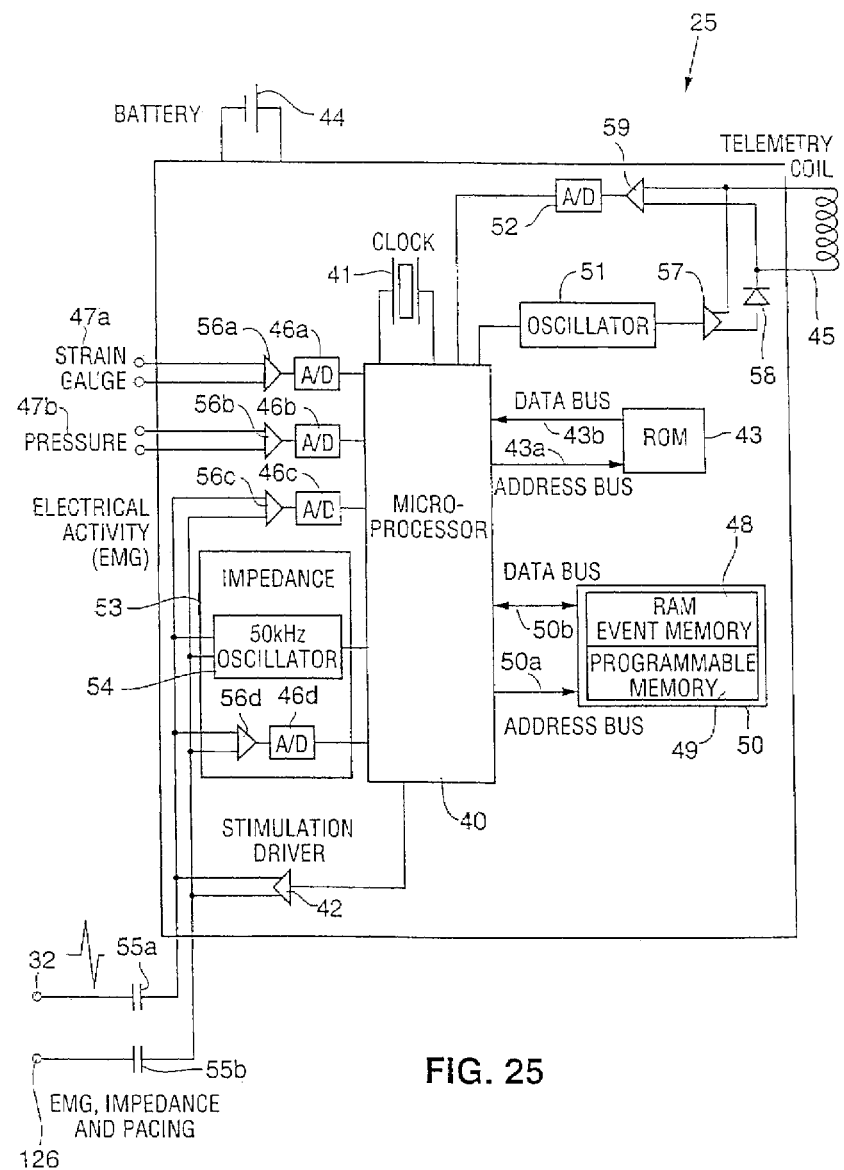
FIG. 25 illustrates a schematic diagram of the circuit of an electronic stimulator of the present invention.

A preferred embodiment of the electronic circuitry 25 is illustrated in FIG. 25. The electronic circuitry 25 of the stimulator is located in the main housing. The circuitry 25 comprises, a microprocessor or controller 40 for controlling the operations of the electronic circuitry 25, an internal clock 41, and battery device 44 such as a pair of lithium iodine batteries for powering the various components of the circuit 25. As such, the controller 40 and battery device 44 are coupled to each of the major components of the circuit as would be apparent to one of ordinary skill in the art. The controller 40 is coupled to stimulation driver 42, which is coupled to stimulating electrodes (e.g., 126, 32 or 245, 246) that are used to provide electrical stimulation in accordance with programmed parameters The controller 40 is coupled to ROM 43, which contains the program instructions for the controller 40 and any other permanently stored information that allows the microprocessor/controller 40 to operate. The controller 40 addresses memory in ROM 43 through address bus 43a and the ROM 43 provides the stored program instruction to the controller 40 via data bus 43b. The controller 40 controls the telemetry coil 45, which communicates with an external control or programming device 60 (FIG. 26), preferably via a modulated RF signal. Processor 40 is coupled to an oscillator 51 that provides an RF signal to be emitted from the telemetry coil 45. The RF signal is preferably at about 500 kHz or higher so that the signal is efficiently transmitted through tissue. The controller 40 controls the oscillator 51 and provides data to be modulated with the RF signal. For example, various sensed data such as pressure, pH, temperature, strain, impedance, electrical activity (EMG) etc., may be delivered through the telemetry coil 45.

The circuit 25 may also be coupled through A/D converters 46a, 46b, 46c, 46d to one or more sensors 47a (e.g., strain gauge), 47b (e.g., pressure), or electrodes 32, 126. Suitable types of these sensors are generally known in the art and may be located within, on, or external to the housing 21 of the main body portion 20. Controller 40 is coupled to RAM 50 via an address bus 50a for addressing a location in RAM 50 and a bidirectional data bus 50b for delivering information to and from RAM memory 50. The RAM memory 50 includes event memory 48 that temporarily stores data recorded by sensors 47a, 47b, 32 and 126 and a programmable memory 49 which may be programmed, for example, by an external programmer 60, to provide treatment protocols, e.g. to specify operating modes such as waveform, frequency, etc. The strain gauge 47a is coupled through A/D converter 46a, which converts the representative electrical signal output by the strain gauge into a digital signal, which is delivered to the microprocessor/controller 40 and stored in the event memory 48 in the RAM 50. The sensor 47b is coupled through A/D converter 46b, which converts the representative electrical signal output by the sensor 47b into a digital signal, which is delivered to the microprocessor/controller 40 and stored in the event memory 48 in the RAM 50. The electrodes 32, 126 are coupled through A/D converters 46c and 46d to the microprocessor 40. A/D converter 46c converts the electrical EMG signal sensed by the electrodes 32, 126 into a digital signal representative of the EMG electrical activity, which is delivered to the microprocessor/controller 40 and stored in the event memory 48 in the RAM 50. Also, the A/D converter 46d converts the electrical signal sensed by the electrodes 32, 126 and provided through the impedance circuit 53 described below, into a digital signal representative of tissue impedance, which is delivered to the microprocessor and stored in the event memory 48 in the RAM 50. The data stored in the event memory 48 may be sent intermittently as data bursts via the telemetry RF coil 45, as opposed to continuously in order to save battery power.

The electrode 32, 126 outputs are used to provide electrical stimulation delivered through the stimulation driver 42 to electrodes. The stimulation modes and parameters can either be set using the external programmer 60, or they may be set in response to sensory feedback. The same electrode outputs are used to sense impedance through impedance circuit 53 and to sense electrical activity which is delivered through driver 56c. The electrodes 32, 126 are coupled through coupling capacitors 55a and 55b respectively, to output of electrical stimulation driver 42 and input of drivers 56c, 56d.

The impedance circuit 53 comprises a constant current source oscillator 54 that oscillates at a frequency of 50-100 kHz, and a driver 56d coupled through A/D converter 46d to the controller 40. The oscillator 54 provides a constant current source through electrodes 32, 126 resulting in a voltage across the electrodes 32, 126 that is representative of impedance, in view of the constant current. The voltage is provided through driver 56d and is converted by A/D converter 46d to a digital signal representative of impedance. Driver 56d has a bandwidth that includes the 50 kHz frequency signal while filtering out the electrical stimulation signal that is delivered to the electrodes 32, 126 through electrical stimulation driver 42, and the EMG signal that is sensed by the electrodes 32, 126. Both of the outputs are filtered out by driver 56d. Driver 56c which delivers the EMG signal to A/D converter 46c, also has a bandwidth that filters out the 50-100 kHz signal. Further, when a stimulation signal is being delivered, the controller 40 does not receive signals from A/D converters 46c and 46d. Thus the EMG and impedance sensing functions and the stimulation deliver functions are separated through the electronic circuitry 25, though using the same electrodes.

Figure 26:
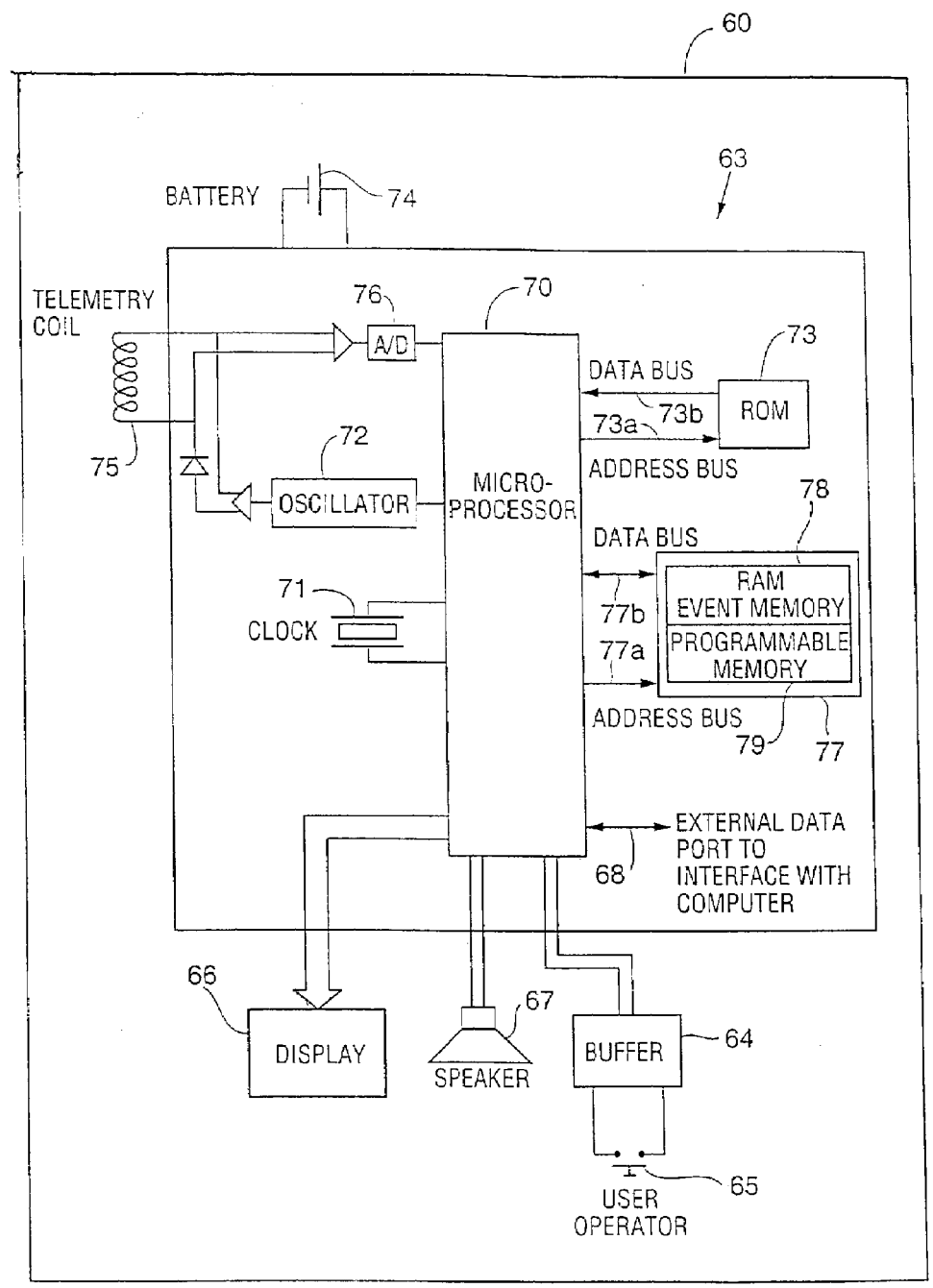
FIG. 26 illustrates a schematic diagram of the circuit of a programmer/recorder of the present invention.

FIG. 26 illustrates the electronic circuitry 63 for external programmer 60. The electronic circuitry 63 comprises: a microprocessor or controller 70 for controlling the operations of the electronic circuitry, an internal clock 71, and a power source 74 such as battery device for powering the various components of the circuit 63. As such, the controller 70 and battery device 74 are coupled to each of the major components of the circuit as would be apparent to one of ordinary skill in the art. The controller 70 is coupled to a speaker 67 for that provides audible alerts and a display 66 such as a CRT to display data such as recorded data, sensed parameters treatment parameters and status of device (e.g. position or battery charge status). The controller 70 is coupled through a buffer 64 to external input device 65 that is used to provide program parameter input, e.g. from a user, for a user to request data displayed in a desired format through display 66 or speaker 67, or to turn device on and off. The external programmer 60 is also provided with an external data port 68 to interface with a computer and provide a means for bi-directional communication of data or commands. The computer may provide programming or data to the controller/microprocessor 70. A user may also interface with the computer to provide treatment protocols or changes in protocols, etc. Also, a user may control the turning on and off of the stimulation program.

The controller 70 is coupled to ROM 73, which contains the program instructions for the controller 70 and any other permanently stored information that allows the microprocessor/controller to operate. The controller 70 addresses memory in ROM 73 through address bus 73a and the ROM 73 provides the stored program instruction to the controller 70 via data bus 73b. The controller 70 controls the telemetry coil 75, which communicates with stimulator electronics 25 (FIG. 25) through its telemetry coil 45. Processor 70 is coupled to an oscillator 72 that provides an RF signal, preferably having a characteristic frequency of 500 kHz or higher, to be emitted from the telemetry coil 75. The controller 70 controls the oscillator 72 and provides data to be modulated with the RF signal, for example, programming information, stimulation parameters, etc. The telemetry coil 75 also receives information transmitted via RF signal from telemetry coil 45 on the stimulator 10 such as various sensed data, e.g., pressure, pH, impedance, electrical activity (EMG) etc. The received RF signal is passed through A/D converter 76 and is transmitted to the controller 70. The data is delivered to the event memory 78 in RAM 77 by way of data bus 77b for temporary storage. The data may be retrieved from RAM 77 by addressing the storage location via the address bus 77a.

Event memory 78 temporarily stores data recorded by sensors 47a-47c and delivered via telemetry to the external programmer 60, until the data is downloaded onto a computer using the external data port 68. The RAM 77 also includes a programmable memory 79 which may be programmed, for example, to specify operating modes such as waveform, frequency, etc which programming is then telemetrically communicated to the stimulation device 10, 210. The modes and parameters can either be set using an external programmer 60 or set in response to sensory feedback.

Figure 27A:
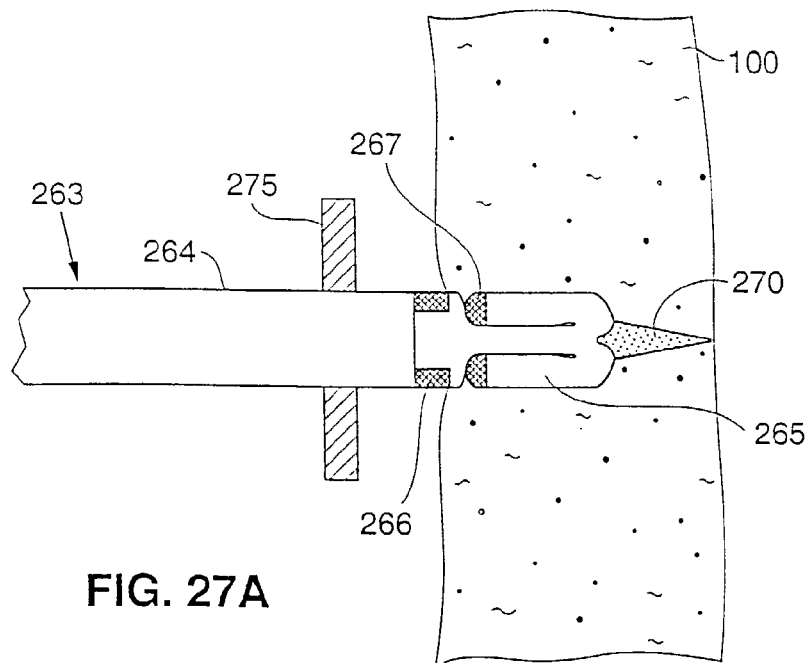
FIG. 27A illustrates a third embodiment of the present invention showing an alternative anchor as it is inserted through the stomach wall.
Figure 27B:
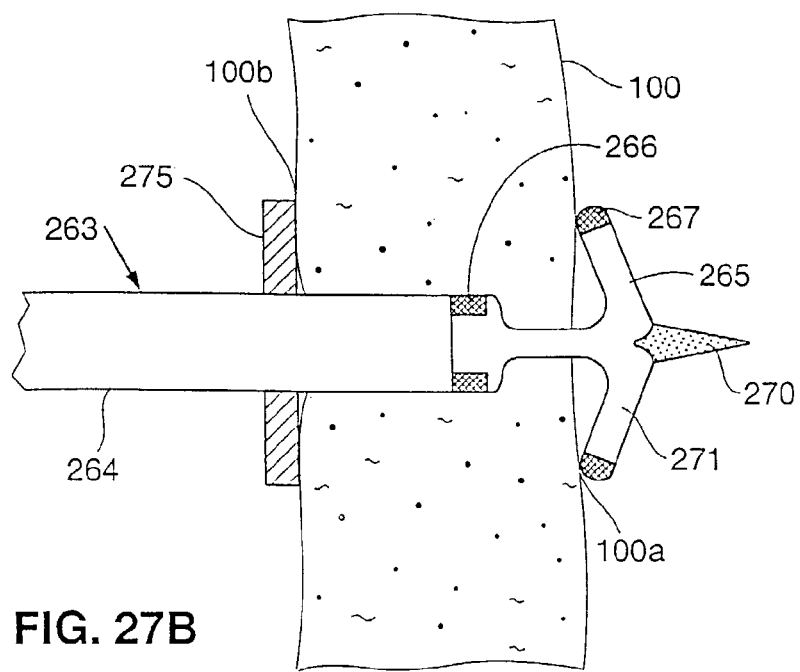
FIG. 27B illustrates the anchor of FIG. 27A anchored to the stomach wall.

FIGS. 27A and 27B illustrate a third embodiment of the present invention showing an anchor device for use with a stimulator or other functional device of the present invention. The anchor 263 comprises an elongate body 264, an expandable distal portion 265 having a sharp tip 270, a bipolar electrode pair 266, 267, and a bumper 275 located on a proximal portion of the elongate body 264. The expandable distal portion 265 comprises a flexible disk 271 for engaging the outer stomach wall. The disk 271 has an inner surface 271a that interfaces with the outer surface 100a of stomach wall 100 and may, for example be coated with an antibiotic material, such as gentamicin sulphate or a silver/silver salts coating such as a powder. The bipolar stimulating electrode pair comprises electrode 266 located on the elongate body 264 and a plurality of electrodes 267 electrically opposite from electrode 266, located at the end of the expandable distal portion 265. The electrodes may be separately coupled to electrical contacts and may be individually selected to provide optimal stimulation pulses, for example, based on contractile response when stimulation pulses are delivered to a particular electrode or electrodes. Electrode 266 is ring extending circumferentially around the elongate body 264. Electrodes 267 are circumferentially spaced from each other around the radial extremity 271b of the disk 271. As an alternative to a plurality of electrodes 267 the electrode located on the disk may be a single ring electrode. Electrodes 266, 267 are electrically coupled to a main body portion containing electronic circuitry (not shown) that is attached in a manner similar to main body portion 20 described above. Conductors 268, 269 electrically couple electrodes 266, 267 respectively to the electronic circuitry of the main body portion.

The anchor 263 may be deployed without requiring an introducer such as described above with reference to FIGS. 4-6. As illustrate in FIG. 27A, the sharp tip 270 is used to pierce the stomach wall 100. The flexible disk 271 folds within recessed portion 265a extending around the distal portion of the anchor 263 so that the disk 271 is flush with the outer surface of the elongate body 264 and forms a taper to the sharp tip 270. The tip 270 is preferably conically tapered so as to atraumatically dilate the stomach wall as it is inserted and help insure a good seal formed by the elastic rebound of the stomach wall tissue around the elongate body 264.

Referring to FIG. 27B as the distal portion 265 of the anchor 263 extends through the stomach wall, the expandable disk 271 opens. The anchor 263 is retracted slightly so that the radial extremity of the disk 271 engages the outer surface 100a of the stomach wall 100, preventing proximal movement of the anchor 263. The electrodes 267 are in electrical contact with the outer surface 100a of the stomach wall. The electrode 266 on the elongate body 264 is embedded within the stomach wall 100 and is in electrical contact with the tissue therein. The bumper 275 may be advanced distally so that is engages the inner surface 100b and secures the anchor 263 in position, preventing distal movement. Preferably the bumper 275 and the disk 271 lock the anchor in place and may also further serve to help seal the opening formed in the stomach from the acidic internal stomach environment and the environment external the stomach wall 100. The bumper 275 may be secured in position by a ratchet mechanism or other means such as a frictional fit. The tip 270 is constructed of a bioabsorbable material such a glucose based absorbable material or polyglycolic acid or polylactic acid, so that the sharp tip 270 readily dissolves and is absorbed by the body, preventing the tip from injuring tissue external to the stomach.

Figure 28A:
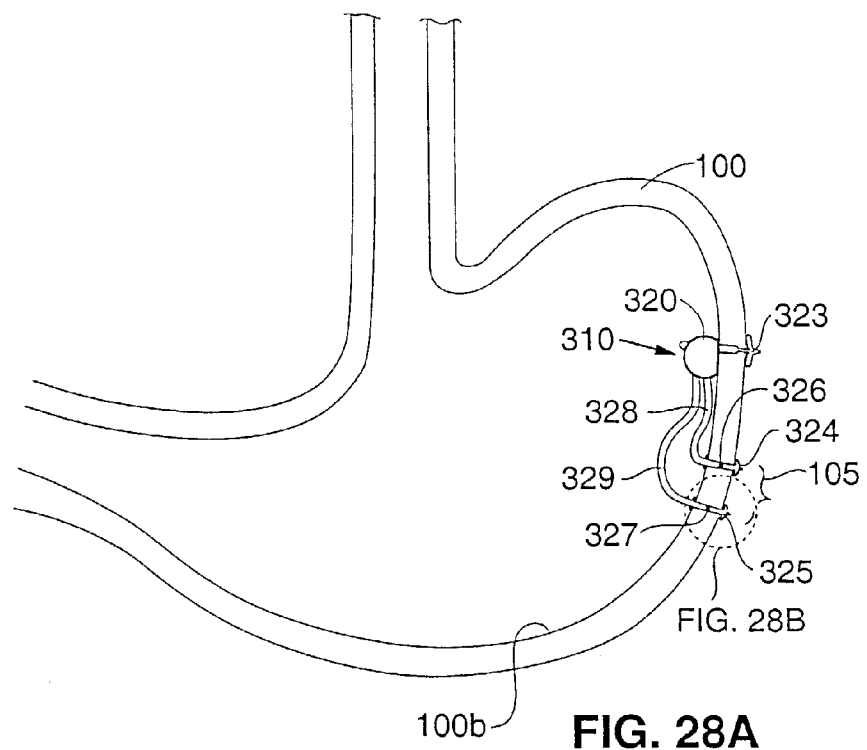
FIG. 28A illustrates a fourth embodiment of the present invention showing an alternative stimulation device.
Figure 28B:
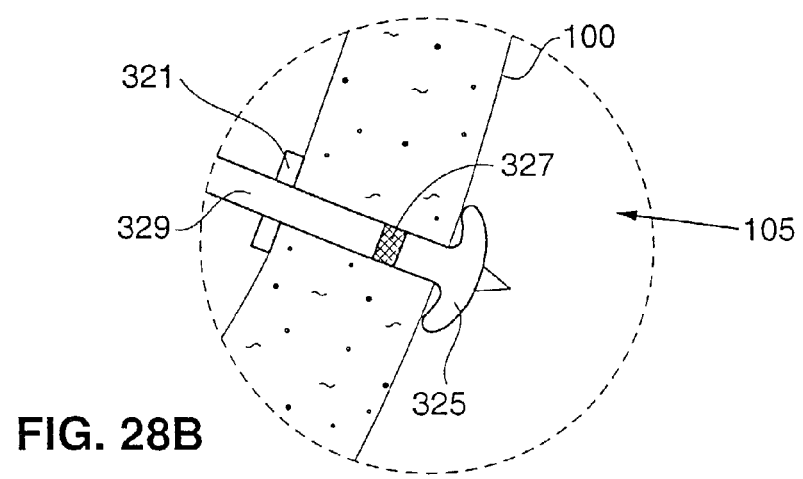
FIG. 28B illustrates an enlarged view of an anchor of the stimulation device of FIG. 28A.

FIGS. 28A and 28B illustrate a fourth embodiment of the present invention showing a stimulator. Stimulator 310 comprises an anchor 323, an electronics unit 320 and electrodes 326, 327 coupled by leads 328, 329 respectively to the electronics unit 320. The stimulator 310 is attached to the inner surface 100b of the stomach wall 100 by anchor 323 which may be constructed or attached in a manner similar to anchors 123, 223, or 263 described above, either with or without electrodes. The electrodes 326, 327 are anchored into the stomach wall 100 with anchors 324, 325 respectively. Referring to FIG. 28B, an anchor 325 is shown deployed in the stomach wall 100. Lead 329 extends from the main body portion 320 through the stomach to the site 105 where stimulation is desired. The anchor 325 is preferably constructed in a manner similar to anchor 263 with a bioabsorbable or resorbable tip and so that the electrode 327 is embedded in the stomach wall 100. The ends of the leads are molded into the housing using corrosion resistant materials suitable for long term use in the stomach. Adjustable sealing ring or bumper 321 operates to prevent anchor 325 from moving out of the stomach and may help to seal the opening in the stomach wall formed by the anchor from the acidic stomach environment and. Anchor 324 is deployed in a similar manner with electrode 326 embedded in the stomach wall 100 at the site 105 for stimulation. Preferably the stimulating electrodes 326, 327 are located at a distance from each other between 5 and 10 mm so that the electrical stimulation is delivered efficiently to the area of interest. The electronic circuitry of the main body 20 delivers electrical stimulation in a manner similar to the stimulation device 10 described above.

Figure 29A:
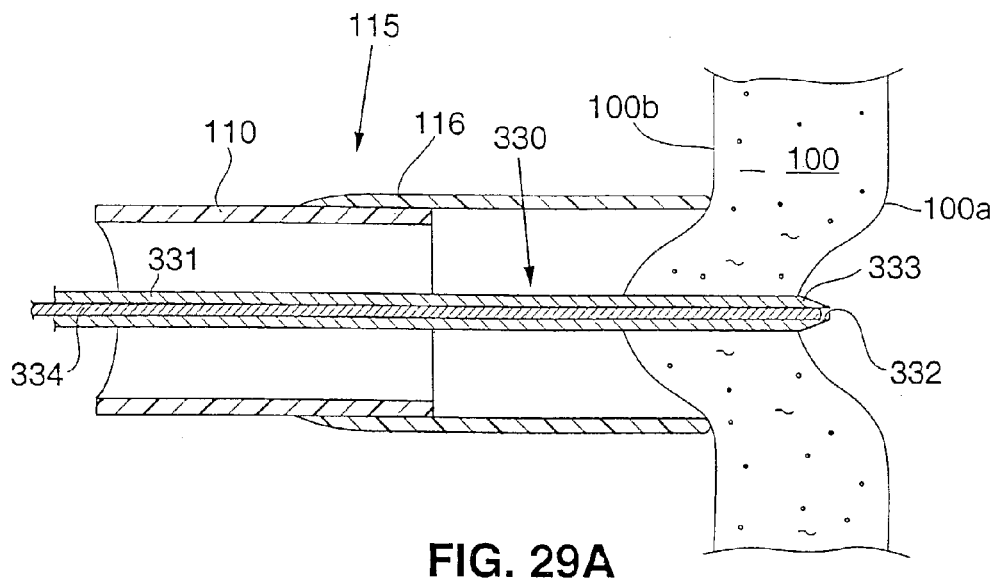
FIGS. 29A and 29B illustrate an alternative endoscopic instrument for placing an attachment device through a stomach wall
Figure 29B:
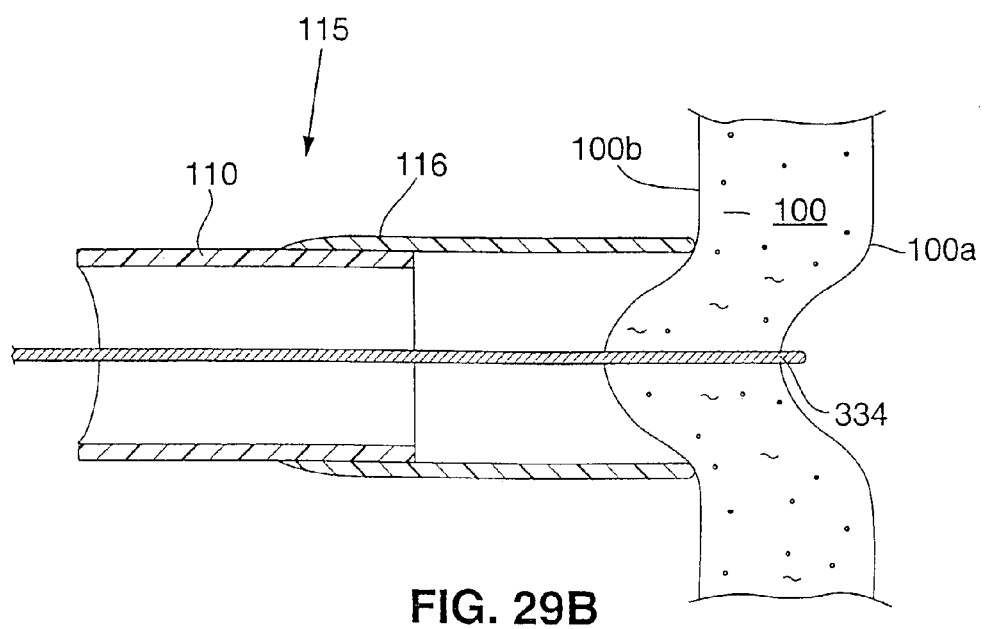

Referring now to FIGS. 29A and 29B, an alternative instrument is illustrated for placing an anchor from the inner surface 100b of the stomach wall 100 through to the outer surface 100a of the stomach wall. The instrument 330 comprises a hollow piercing needle 331 having a lumen 332 therethrough and a stomach piercing tapered distal end 333. A guide wire 334 extends through the lumen 332 in the needle 331. The needle 331 is relatively stiff to allow it to pierce the stomach wall while the guide wire 334 is more flexible. As illustrated in FIG. 29A, the distal end 115 of the endoscope is located at a desired site on the inside 100b of the stomach wall 100. A vacuum pressure is applied to the wall to stabilize it and the needle 331 pierces the stomach wall through a single point, preferably in a direction that is substantially perpendicular to the natural orientation of the stomach wall to prevent folding of the stomach wall and tearing forces during smooth muscle contraction, at the point of attachment. As illustrated in FIG. 29B, the needle 331 is removed, leaving the guide wire 334 in place. Preferably, the instrument 330 is inserted through the auxiliary channel 114 in the endoscope or through a channel 111a or 111b in the over tube 111 and then is located to the desired site using the endoscope 110 for visualization.

Figure 30A:
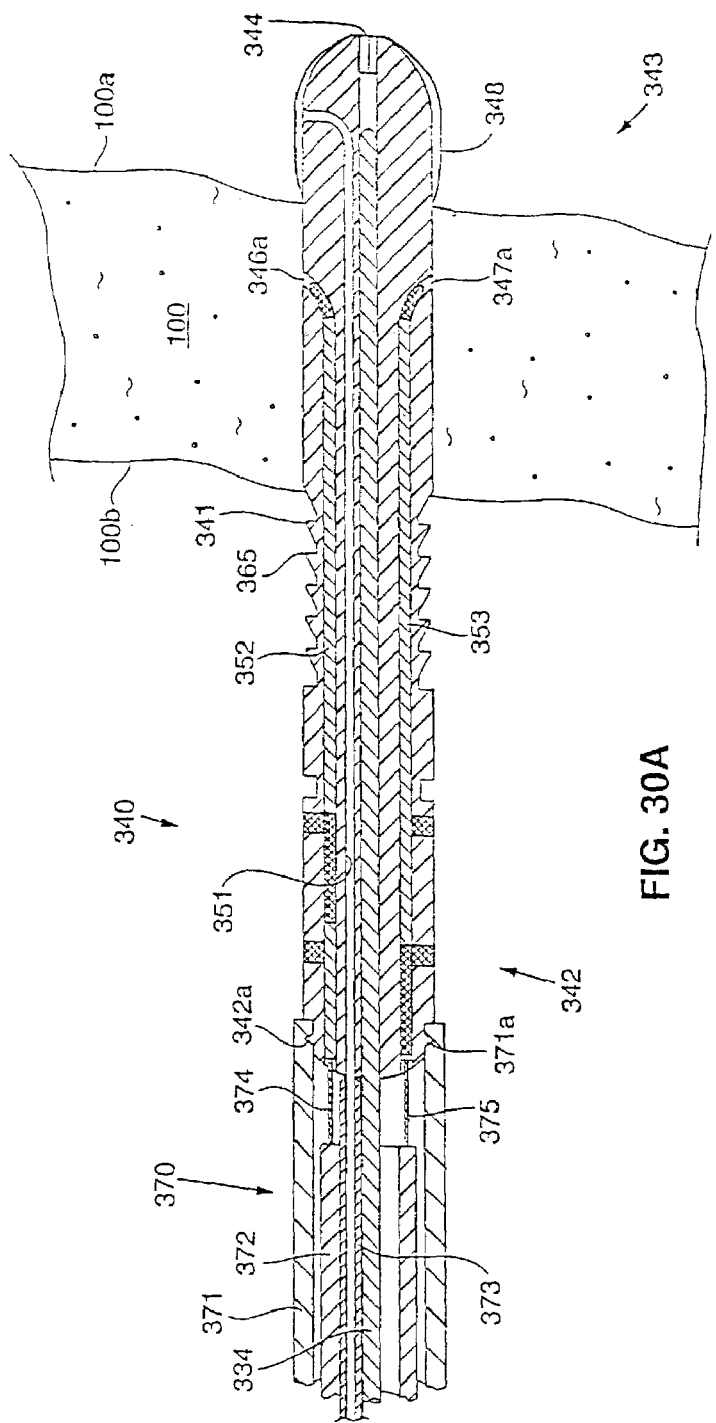
FIGS. 30A and 30B illustrate a fifth embodiment of present invention in which an anchor is placed using the instruments of FIGS. 29A and 29B.
Figure 30B:
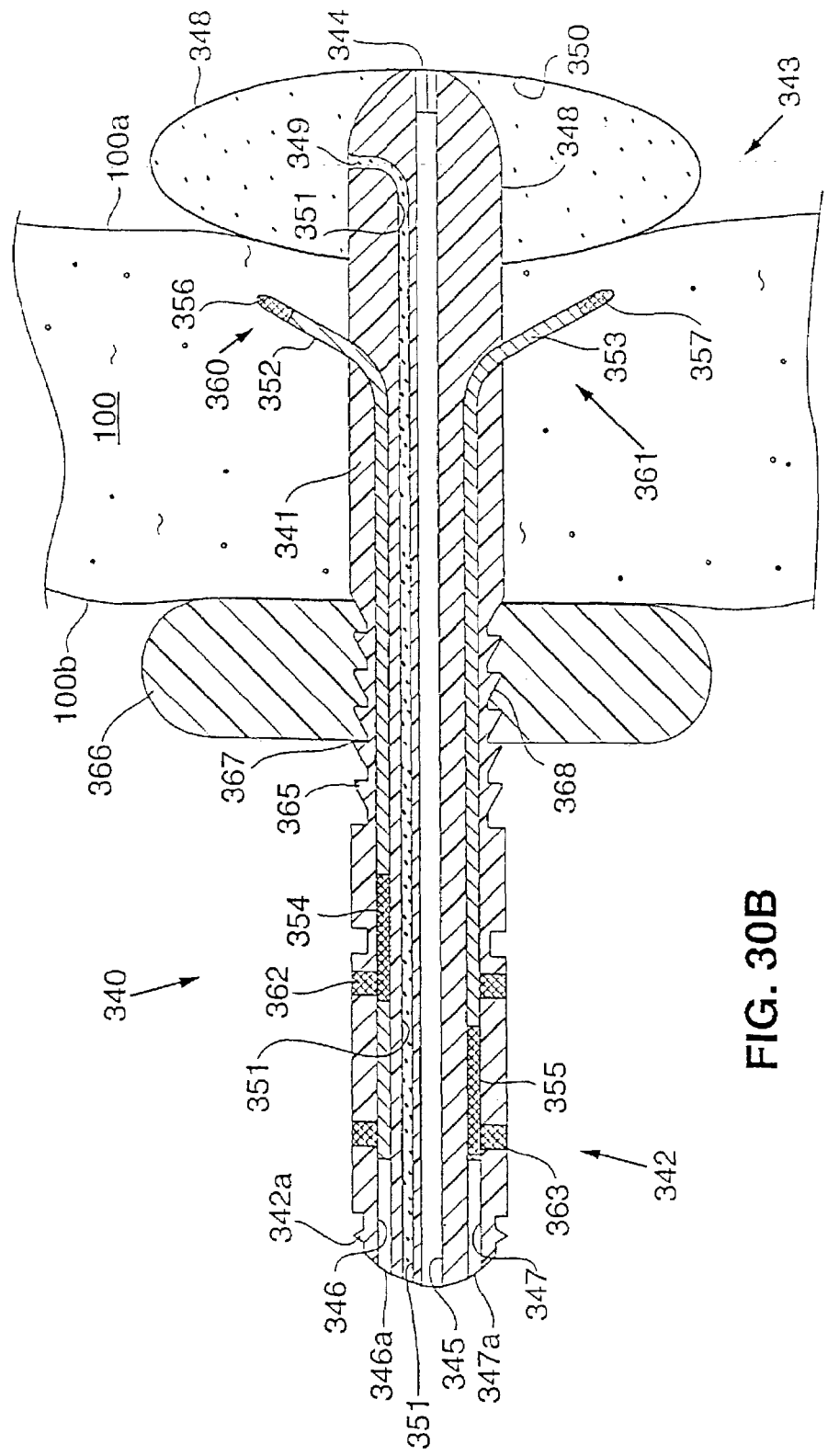

Referring to FIGS. 30A and 30B, an anchor 340 is illustrated placed into the stomach wall 100 over the guide wire 334. The anchor 340 includes an elongate member 341 that is to be placed through the stomach wall 100 in a direction substantially perpendicular to the stomach wall. The anchor 340 has a distal portion 343 that is to at least partially extend through the stomach wall, and a proximal portion 342 having a threaded proximal end 342a for engaging with a threaded end of an instrument used to advance the anchor 340 into place. The anchor 340 includes a guide wire lumen 345 extending through the anchor 340 from the proximal portion 342 to the distal portion 343 with an opening in the proximal portion 342 and distal portion 343 for receiving the guide wire 334 of the insertion instrument 330. As shown in FIG. 30A, the anchor 340 is inserted over the guide wire 334 which guides the anchor 340 into position through the stomach wall 100. The guide wire lumen 345 at the distal portion 343 of the anchor 340 is sealed with a self-sealing plug 344 formed of an elastomer and having a slit along the plug 344 so that the guide wire 334 can open the plug 344 while the guide wire 334 extends through the lumen 345.

An expandable member 348 is located on the distal portion 343 of the anchor 340. The expandable member 348 comprises a balloon formed of either a compliant or non-compliant material such as, e.g., polyurethane, polyethylene or polyester bonded to the outer surface of the distal portion 343 of the anchor 340 and providing an inflation chamber 350. Accordingly, the balloon may be inflated to a predetermined pressure (typically using a non-compliant material) or a predetermined volume (typically using a compliant material). An inflation lumen 351 extends from an opening in the proximal portion 342 to an opening 349 in the distal portion 343. The opening 349 in the inflation lumen 351 is in fluid communication with the inner chamber of the expandable member 348 so that an inflation medium may be supplied through the inflation lumen to inflate the expandable member 348. As illustrated in FIG. 30B, the anchor 340 is placed in the stomach wall and the expandable member 348 is inflated by supplying the inflation chamber 350 with an inflation medium. In a preferred embodiment, a curable elastomeric polymer is used as an inflation medium, e.g., a two-part curable elastomeric polymer mixed just prior to delivery through the inflation lumen 151. The polymer thus allows the balloon to conform to the outer stomach wall and surrounding tissue to secure the anchor 340 to outer surface 100a of the stomach wall. The balloon is preferably designed and the inflation medium is selected to provide an inflated distal end that is sufficiently firm to secure the anchor 340 in place while having sufficient surface area and being malleable enough that the anchor is sealed into place in a relatively atraumatic manner.

The anchor 340 further comprises ratchets 365 on the outer circumference of the elongate member 341 and a sealing bumper ring 366 having an opening 367 forming an inner circumferential wall with ratchet teeth 368 for engaging the ratchets 365 on the elongate member 341. The bumper ring 366 is moveable in a distal direction to sealingly secure the anchor 340 to the stomach wall and prevent distal movement of the anchor 340. The bumper ring 366 preferably has sufficient surface area and is formed of an elastomer that spreads the load and minimizes friction or other trauma to the stomach wall.

The anchor 340 further comprises electrode lumens 346, 347 having openings 346a, 347a in the elongate member 341. Conductor members 352, 353 extend through the electrode lumens 346, 347, respectively, and include flexible conductors insulated along their length. The flexible conductor members 352, 353 are preferably constructed of an elastic or superelastic alloy with an insulative coating. Electrically opposite electrodes 356, 357 are located on distal portions 360, 361 of moveable flexible conductor members 352, 353 respectively. Exposed electrical contacts 354, 355 are located on the proximal portions of the conductor members 352, 353. The electrical contacts 354, 355 are in electrical contact with contacts 362, 363 respectively that are electrically coupled to contacts in a main body of a stimulator unit in a manner similar to the sealing electrical connection of main body 20 and anchor 123 described herein. The adjustable electrodes 356, 357 are contained within the electrode lumens 346, 347 when the anchor 340 is initially placed as illustrated in FIG. 30A. The adjustable electrodes 356, 357 are deployed within the stomach wall 100 by advancing the conductors members 352, 353 distally through the electrode lumens 346, 347 where the openings 346a, 347a are configured to direct the electrodes 356, 357 laterally from each other and within the stomach wall as illustrated in FIG. 30B. The electrodes 356, 357 are moved with respect to one another into a selectable optimal deployment position with an optimal distance between the electrodes 356, 357.

An endoscopic instrument 370 is used to place the anchor 340, inflate the expandable member 348 and deploy the electrodes 356, 357. The instrument 370 is preferably used through the overtube 111, an opening 111a or 111b in the overtube 111 and/or through an instrument channel 114 in the endoscope 110 (while the procedure is visualized through the endoscope 110.) The instrument 370 includes an inflation tube 373 removably attached to the inflation lumen 351 of the anchor 340. The inflation tube 373 forms a continuous conduit with the inflation lumen 351 a conduit through which an inflation medium is supplied to inflate the expandable member 348. A push tube 371 comprises a threaded end 371a that engages the proximal end 342a of the anchor 340. The push tube 371 is used to advance the anchor 340 over the guide wire 334. An inner tube 372 includes prongs 374, 375 that engage the conductor members 352, 353 and are used to advance the electrodes 356, 357 into the stomach wall by pushing the inner tube 372 while holding the anchor 340 in place with the push tube 371. The prongs 374, 375 comprise electrically conductive wires that extend within the insulative material of the inner tube 372 to a stimulator/sensor circuit located externally of the patient's body. The stimulator/sensor may be used to deliver test stimulation pulses to the stomach wall through the electrodes 356, 357 or to measure the impedance of the stomach wall tissue between the electrodes 356, 357. (e.g. to determine sufficient response to stimulation, sense electrical activity). The stimulation response may be determined by observing through the endoscope, contractions of the stomach wall, or by determining contractions using one or more sensors, e.g. as described with respect to the various embodiments herein.

After the anchor 340 is in place, an inflation medium is supplied through the inflation tube 373 to inflate the expandable member 348 adjacent the outside 100a of the stomach wall. The inflation tube 373 has a thin walled region at its distal end where it joins the inflation lumen 351. After the expandable member 348 is inflated, the inflation tube is removed by twisting or pulling the tube to break it away from the anchor 340. The push tube 374 serves to hold the anchor 340 into place in the stomach wall as the inflation tube 373 is disengaged. The bumper ring 366 is then advanced distally to engage the inner wall of the stomach with ratchets 365 engaging ratchets 368 to prevent further distal movement of the anchor through the stomach wall. After the anchor 340 is in place, the push tube 371 may be removed by unthreading the end 371a on the push tube 371 from the threaded end 372a of the anchor 340. A stimulator unit such as the main body portion 20 described herein is coupled to the anchor 340 in a manner similar to that described herein with reference to anchor 123 with electrical contacts 354, 355 coupled to the electronics unit within the stimulator through electrical contacts 362, 363. Electrical contacts 362, 363 are to be coupled to a stimulator unit in as similar manner as are contacts 28, 28a, or 28b described herein.

Alternatively the laterally extending conductive members 352, 353 may be used to secure the anchor to the stomach wall without requiring an additional expandable distal portion.

Figure 31A:
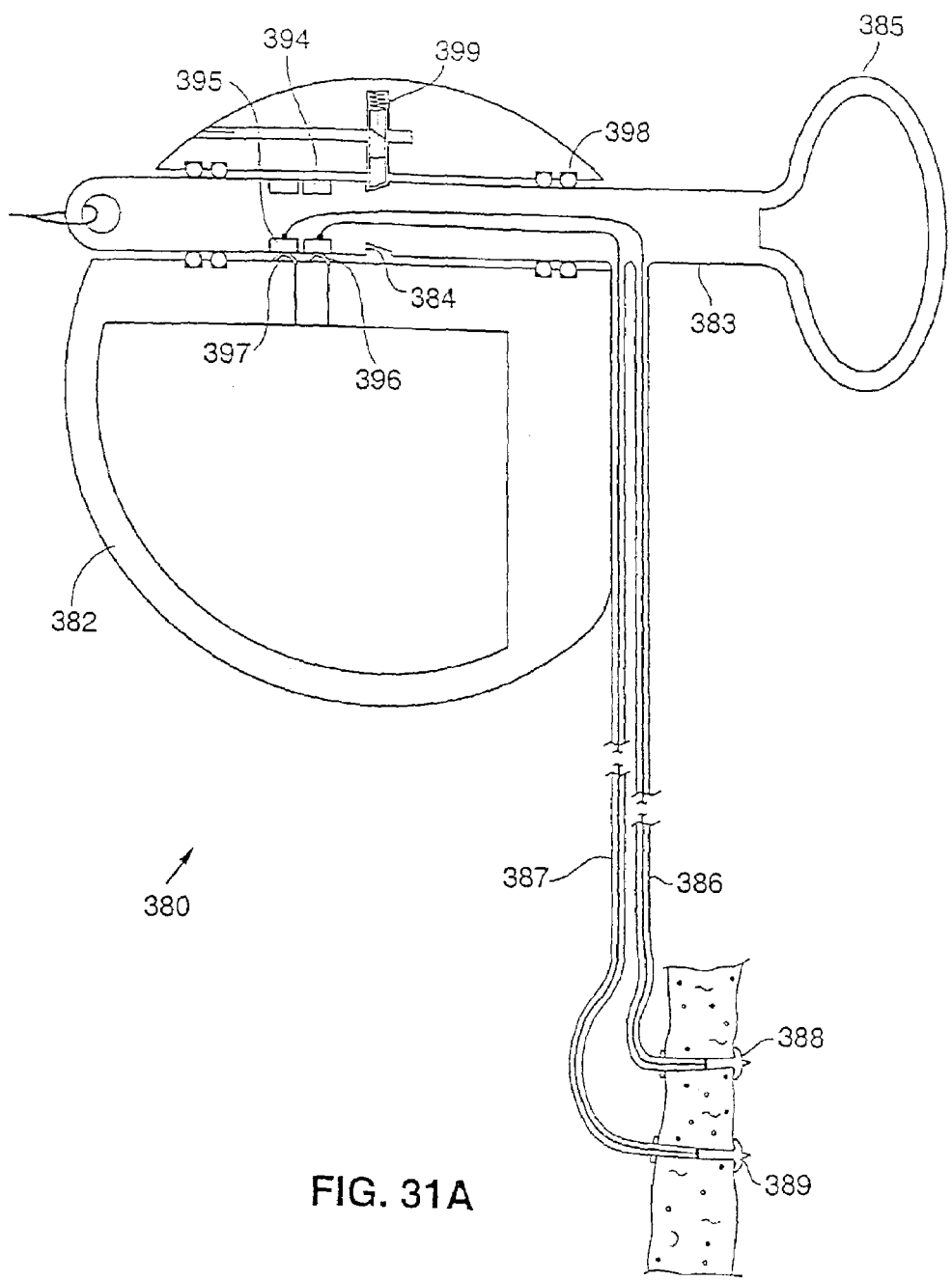
FIGS. 31A illustrates a sixth embodiment of the present invention including an anchor and stimulator
Figure 31B:
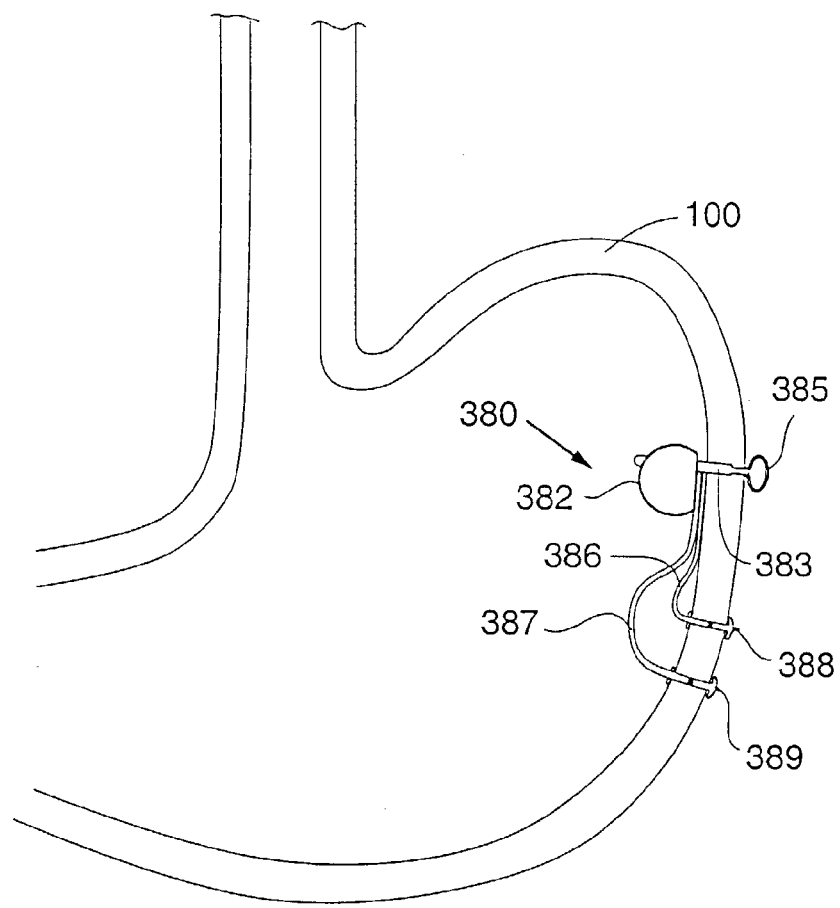
FIG. 31B illustrates the anchor and stimulator of FIG. 31B attached within the stomach.

Referring to FIGS. 31A and 31B an alternative stimulator 380 is illustrated comprising a main body portion 382 and an anchor 383. The anchor 383 includes an expandable distal end 385 for securing the anchor to the stomach wall, seals 398 for sealing the anchor electrical contacts 394, 395 and electrical contacts 396, 397 of the housing from the acidic environment of the stomach. A notch 384 in the anchor is arranged to engage a latch 399 in the main body 382 to couple the anchor 383 and the main body 382 together so that contacts 396, 397 of the housing 382 are in electrical contact with anchor contacts 394, 395, respectively. The anchor 383 further comprises insulated flexible conductors 386, 387 extending from the anchor 383. The conductors 386, 387 are coupled to electrode anchors 388, 389 that are constructed and attached to the stomach wall in a manner similar to the anchors 324, 325 described herein with reference to FIGS. 28A and 28B.

Figure 32:
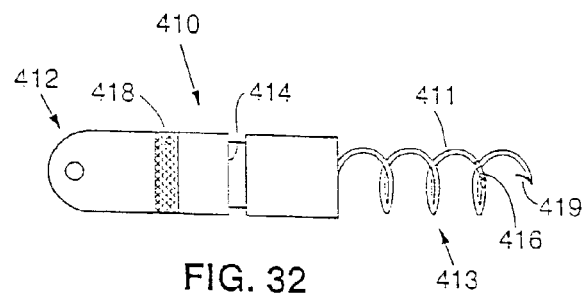
FIG. 32 illustrates a seventh embodiment of the present invention including a screw in attachment device.

FIG. 32 illustrates an alternative embodiment of an anchor device of the present invention. Anchor 410 comprises a screw connector 411 located on the distal end 413 of the anchor 410. The screw 411 includes electrode 416 coupled by way of a conductor extending through the anchor 410 to electrical contact 418. The distal portion of the screw may include a retaining element 419 to prevent dislodgement of the screw from the stomach wall. The anchor 410 includes a notch 414 for engaging a latch in a stimulator unit similar to the main body 20 described herein, so that the electrical contact 418 is in electrical contact with a stimulator unit electrical contact similar to contact 28, 28a, or 28b of a main body 20 described herein. An endoscopic instrument engages the proximal end 412 of the anchor 410 and rotates the anchor 410 so that it is secured to a stomach wall.

Figure 33A:
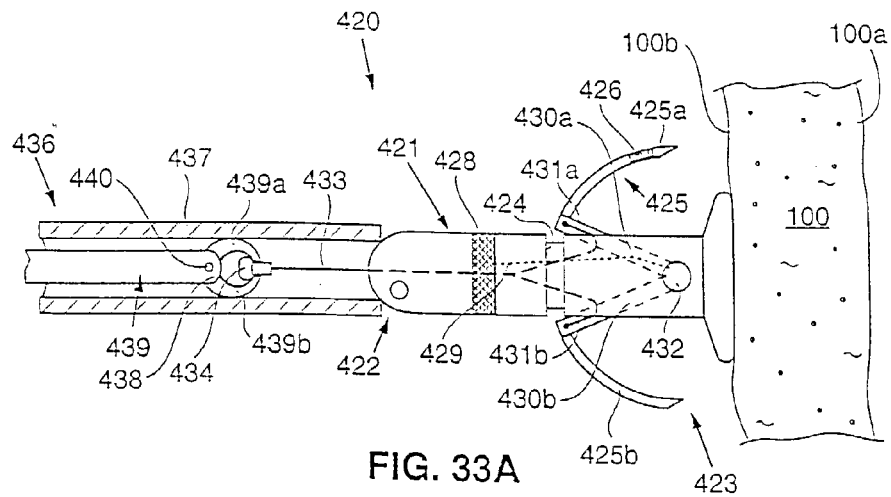
FIGS. 33A and 33B illustrate an eight embodiment of the present invention including an anchor with a clip on attachment device.
Figure 33B:
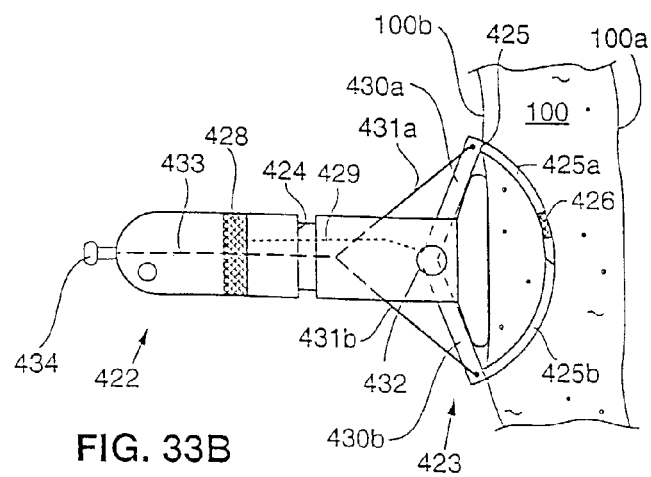

FIGS. 33A and 33B illustrate an alternative embodiment of an anchor of the present invention. Anchor 420 comprises an elongate body 421 having a proximal portion 422 and a distal portion 423. Anchor also includes a notch 424 and electrical contact 428 located on the elongate body 421. The notch 424 is arranged to couple the anchor to a stimulator unit such as main body 20 described herein so that the electrical contact 428 is in electrical communication with an electrical contact on the housing such as contacts 28, 28a, or 28b, described herein. Anchor 420 also comprises a clip 425 consisting of prongs 425a and 425b, preferably constructed of titanium with an insulative coating. An exposed electrode area 426 is located on prong 425a. The prong 425a is coupled by way of electrical conductor 429 to electrical contact. The prongs 425a, 425b are coupled to lever arms 430a, 430b that rotate about spring loaded hinge 432 so that the prongs 425a, 425b tend towards a closed position as illustrated in FIG. 33B. Wires 431a, 431b (or strings) are attached to the lever arms 430a, 430b respectively. Wires 431a, 431b are also attached to an actuating wire 433 that extends through the proximal portion 422 of the anchor 420 where it is attached to a handle 434. The handle 434 may be retracted in a proximal direction to pull on the lever arms 430a, 430b to open the clip 425 as illustrated in FIG. 33A. When the handle 434 is released, the spring load clip 425 tends to close as shown in FIG. 33B so that the prongs 425a, 425b are secured within the stomach wall. As shown in FIG. 33A an endoscopic instrument 436 comprising a push tube 437 and a grasper 438 is used to attach the clip 425 to the stomach wall. The push tube 437 engages the proximal portion 422 of the anchor 420 to advance the anchor to a site for attaching the anchor to the stomach wall. A grasper 438 extends through the push tube and includes a grasping end effector 439 having grasping arms 439a and 439b that rotate about hinge 440 which is coupled to an actuating device extending through the push tube 437 out of the patient's mouth. The grasping arms are used to grasp the handle 434 of the anchor and the grasper 438 is retracted from the push tube 437 to pull the handle to open the clip, as illustrated in FIG. 33A. The clip 425 is advanced to the site on the stomach wall for attachment. The handle 434 is then released so that the prongs 425a and 425b engage the stomach wall with electrode 426 in electrical contact with the wall. A stimulator unit may then be attached to the anchor in a manner similar to the attachment of anchor 123 and main body 20 described herein.

Figure 34A:
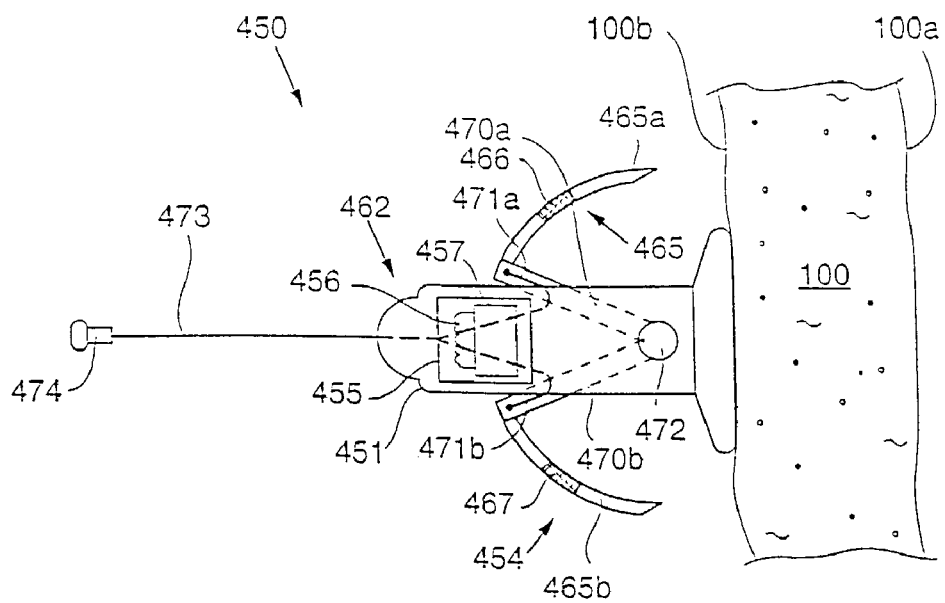
FIGS. 34A and 34B illustrate a ninth embodiment of the present invention including an inductively powered stimulation device.
Figure 34B:
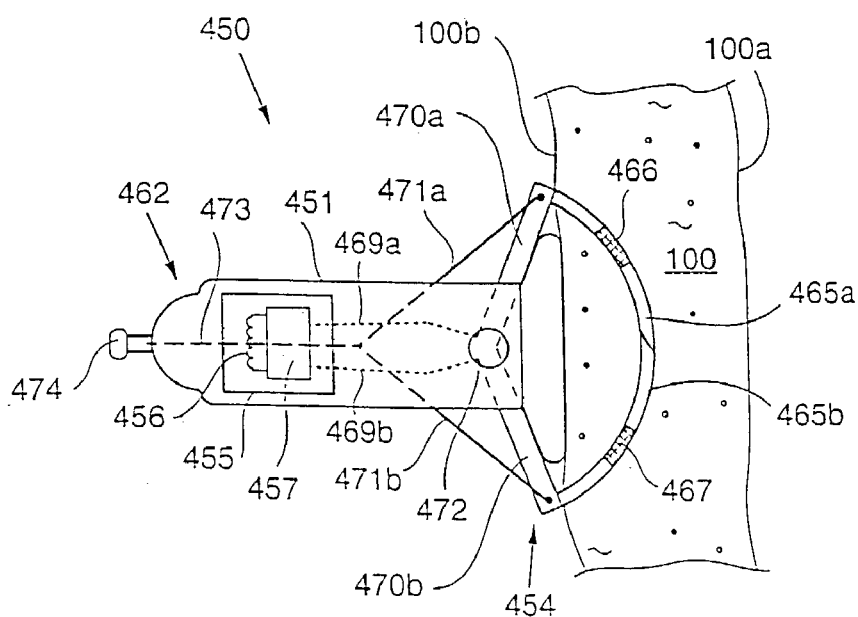

Referring now to FIGS. 34A and 34B an alternative device is illustrated for attachment to the wall of the stomach or other organ. The device 450 comprises an electronics unit 455 located in a main body portion 451. The device further comprises an attachment device 454 for attaching the main body portion 451 to the inside 100b of the stomach wall 100. The attachment device 454 comprises a clip 465 consisting of prongs 465a and 465b. The prongs 465a and 465b include one or more sensors or therapeutic devices located thereon. Preferably, the sensor or therapeutic devices comprises electrodes 466 and 467 located on prongs 465a, and 465b respectively. The prongs 465a and 465b are preferably constructed of titanium with an insulative coating. The prongs 465a 465b are coupled by way of electrical conductors 469a, 469b respectively to electronics unit 455. The prongs 465a, 465b are coupled to lever arms 470a, 470b that rotate about spring loaded hinge 472 so that the prongs 465a, 465b tend towards a closed position illustrated in FIG. 34B. Wires 471a, 471b (or strings) are attached to the lever arms 470a, 470b respectively. Wires 471a and 471b are also attached to an actuating wire 473 that extends through the proximal portion 462 of the device 450 where it is attached to a handle 474. The handle 474 may be retracted in a proximal direction to pull on the lever arms 470a, 470b to open the clip 465 as illustrated in FIG. 34A. When the handle 474 is released, the spring load clip 465 tends to close as shown in FIG. 34B so that the prongs 465a, 465b are secured within the stomach wall. An endoscopic instrument may be used to place the device 450 or to remove the device, by manipulating the handle 474.

The electronics unit 455 comprises an electromagnetic coil 456 for inductively receiving power from an external source. The electromagnetic coil 456 is coupled to a voltage regulating circuit 457, which is coupled to electrodes 466, 467. The voltage regulating circuit 457 operates to convert a high frequency AC signal to a regulated voltage signal that acts as a stimulation burst delivered to the stomach wall through electrodes 466, 467. Stimulation pulses in accordance with a stimulation program may be supplied to the electrodes 466, 467 which may act as electrically opposite bipolar electrodes. A plurality of devices 450 may be placed in various locations in the stomach wall. Preferably each device has electronics operating at a frequency different from the other devices or operating at the same frequency but responding to digital commands that are different for each device, so that the stimulation program may selectively stimulate various locations in the stomach. Additionally or alternatively, the devices 450 may act as sensors sensing electrical characteristics of the stomach wall. Also, other passive sensors may be located on the device. The sensors may sense a parameter of the stomach wall and transmit a representative signal to an external device via the electromagnetic coil when prompted by an external power signal.

Figure 35A:
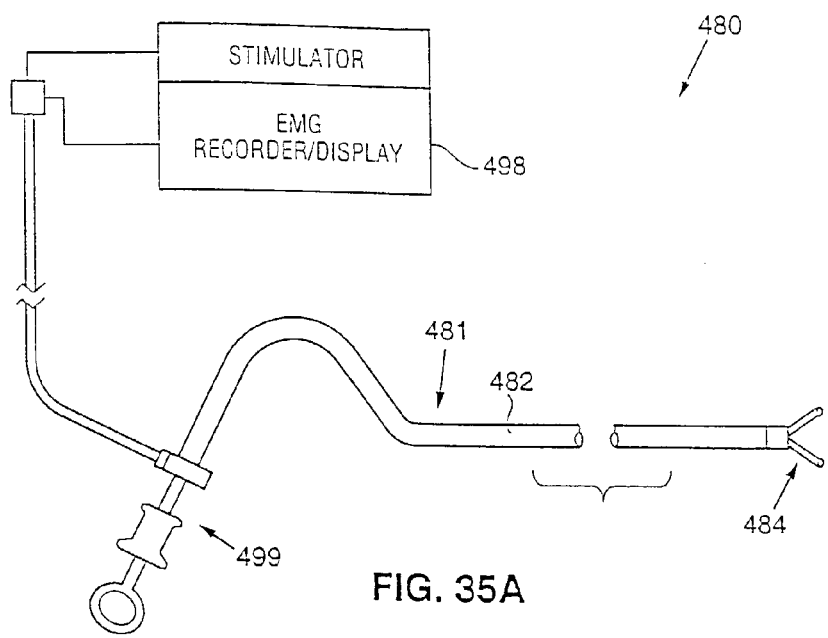
FIGS. 35A and 35B illustrate a tenth embodiment of the present invention including an endoscopic tool for mapping electrical activity in the stomach.
Figure 35B:
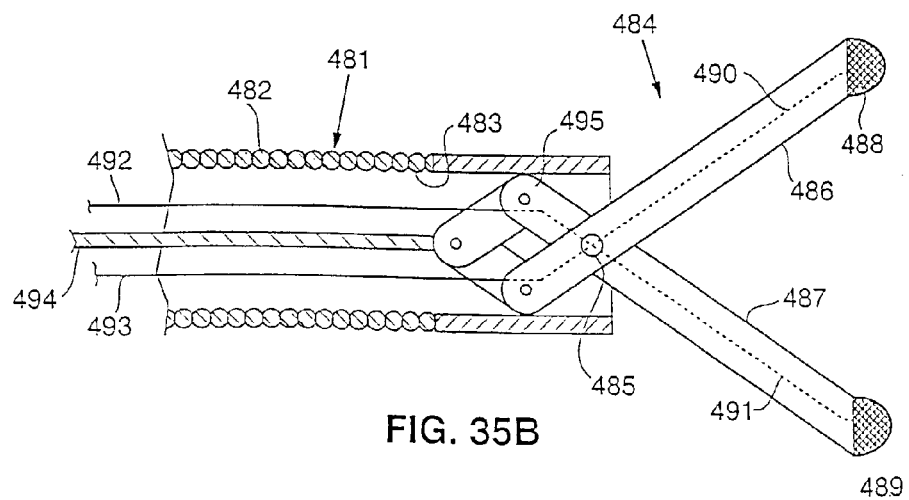

Referring to FIGS. 35A and 35B, an endoscopic instrument 480 is used to map electrical activity in the stomach wall and to identify and characterize the response of the stomach wall to various electrical stimulation parameters. The instrument 480 comprises an elongate flexible member 481 generally formed of a coil 482 with a lumen 483 extending therethrough. An end effector 484 is located at the distal end of the instrument 480. The end effector 484 comprises electrode members 486, 487 coupled together by a hinge 485. The electrode members 486, 487 include electrodes 488, 489 located at the ends of the members 486, 487. The electrodes 488, 489 are coupled through conductors 490, 491 extending through electrode members 486, 487 to wires 492, 493 which extend through the lumen 483 in the instrument 480 to a proximally located handle 499. The wires 492, 493 are coupled to an external stimulator/recorder unit 498, which supplies stimulation energy to electrodes 488, 489 through wires 492, 493 and records electrical activity sensed by the electrodes through the wires 492, 493. A mechanical wire 494 is coupled to a hinge actuating device 495 and extends through the lumen 483 to handle 499. The electrode members 486, 487 are initially in a closed position. When the wire 494 is moved distally using handle 499, the hinge actuating device 495 rotates the electrode members 486, 487 about hinge 485 to spread the electrode members 486, 487 and electrodes 488, 489 apart from each other. In this position (FIG. 35B), the electrodes may be placed on the stomach wall at a desired site to measure and record electrical activity, electrical parameters, or to provide electrical stimulation pulses to the stomach wall. Upon providing stimulation pulses to the stomach wall, the response of the stomach (e.g., the presence, absence or degree of contraction) may be observed, either visually or through a sensor (not shown) located on the end effector 484 that senses muscle contractions, such as, for example, a strain gauge. The ideal location for attaching a stimulation device may be determined by sensing electrical activity, electrical parameters or by observing a location where stimulation results in a desired response. Also the ideal stimulation parameters or program may also be determined with the device by observing the response of a site to various stimulation parameters delivered by the end effector 484.

The materials of the attachment devices, stimulators and housings of the present invention are preferably selected for long-term use in the stomach, i.e., two or more years. Suitable materials include the materials described herein, such as those described with respect to the construction of the main body 20.

The invention has been described with reference to preferred embodiments and in particular to a gastric stimulator, the present invention contemplates that the attachment devices may be used to attach a number of functional devices to the wall of the stomach for sensing parameters of the stomach or its environment, or for diagnosing or providing treatment to the stomach. The attachment device may incorporate such sensing, diagnostic or treatment devices within the attachment device. Such functional devices may also be separately attached to the stomach and/or to the attachment device or to another functional device. The attachment device or functional devices may communicate to an external recorder or controller by way of telemetry. They may be battery powered or powered by inductive coupling. A plurality of functional devices may be attached to the stomach wall. The functional devices may be programmed to respond to information or signals delivered by other functional devices whether the signals are delivered from one device to another through conductors or whether the signals are delivered, e.g. through the stomach wall or medium within the stomach.

It is also contemplated that instruments described herein to attach or remove the attachment devices and stimulators may be used to attach and remove a variety of functional devices or to perform a number of different endoscopic procedures. Alternative mechanisms for attaching the various elements to the stomach wall are also contemplated, including for example staples, sutures and other means.

While the invention has been described with reference to preferred embodiment, it will be understood that variations and modifications may be made within the scope of the following claims. Such modifications may include substituting elements or components which perform substantially the same function in substantially the same way to achieve substantially the same result that the invention can be practiced with modification within the scope of the following claims.

What is claimed is:

1. A system for performing diagnostic or therapeutic functions at a stomach comprising:
    a functional device which performs the diagnostic or therapeutic functions, the functional device comprising implantable circuitry and a battery packaged so as to allow the functional device to generate diagnostic or therapeutic signals from within the stomach; and
    an attachment device configured for attaching the functional device to the stomach so as to mechanically support the functional device within the stomach, the attachment device comprising,
        a securing element device comprising a first portion at least a portion of which is arranged to extend through the stomach wall, and having first and second surfaces oriented for engaging inner and outer surfaces of the stomach wall when implanted so as to secure the attachment device to the stomach wall, and
        a coupling element arranged to receive and couple the functional device to the attachment device after the attachment device has been secured to the stomach wall.

2. The system of claim 1, wherein said attachment device is removably attachable to the functional device.

3. The system of claim 1 wherein said attachment device further comprises a releasable latching mechanism.

4. The system of claim 1 wherein said coupling device includes a quick release mechanism.

5. The system of claim 1 wherein said first portion is configured to extend through said stomach wall in an orientation substantially perpendicular to said stomach wall.

6. The system of claim 1 wherein said first portion comprises a strain gauge located thereon.

7. The system of claim 1 further comprising at least one lateral extending member arranged to be deployed to extend laterally of the first portion within the stomach wall.

8. The system of claim 7 wherein said at least one laterally extending member is configured to secure the attachment device to the stomach wall.

9. The system of claim 7 wherein said at least one laterally extending member comprises an electrode located thereon.

10. The system of claim 1 wherein said attachment device is removably attachable to said stomach wall.

11. The system of claim 1 wherein said first portion comprises a distal end having a sharp tip located thereon.

12. The system of claim 11 wherein said tip comprises a bioabsorbable material.

13. The system of claim 1 wherein said securing element comprises a clip.

14. The system of claim 13 wherein said clip is spring loaded.

* * * * *